United States Patent
Gilman et al.

(10) Patent No.: US 9,421,391 B2
(45) Date of Patent: *Aug. 23, 2016

(54) COORDINATED MEDIUM VOLTAGE THERAPY FOR IMPROVING EFFECTIVENESS OF DEFIBRILLATION THERAPY

(71) Applicant: Galvani, Ltd., Edina, MN (US)

(72) Inventors: Byron Gilman, Edina, MN (US); Mark Kroll, Crystal Bay, MN (US)

(73) Assignee: Galvani, Ltd., Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/727,343

(22) Filed: Jun. 1, 2015

(65) Prior Publication Data

US 2015/0367138 A1  Dec. 24, 2015

Related U.S. Application Data

(63) Continuation of application No. 14/259,892, filed on Apr. 23, 2014, now Pat. No. 9,061,164, which is a continuation of application No. 13/712,683, filed on Dec. 12, 2012, now Pat. No. 8,750,990.

(51) Int. Cl.
  *A61N 1/39* (2006.01)
  *A61N 1/36* (2006.01)
  *A61N 1/362* (2006.01)

(52) U.S. Cl.
  CPC .......... *A61N 1/3987* (2013.01); *A61N 1/36003* (2013.01); *A61N 1/3621* (2013.01); *A61N 1/3918* (2013.01); *A61N 1/3925* (2013.01); *A61N 1/3962* (2013.01)

(58) Field of Classification Search
None
See application file for complete search history.

(56) References Cited

U.S. PATENT DOCUMENTS

| | | |
|---|---|---|
| 3,638,656 A | 2/1972 | Grandjean et al. |
| 3,703,900 A | 11/1972 | Holznagel |
| 3,923,060 A | 12/1975 | Ellinwood, Jr. |
| 3,952,750 A | 4/1976 | Mirowski et al. |
| 3,978,865 A | 9/1976 | Trabucco |
| 4,003,379 A | 1/1977 | Ellinwood, Jr. |

(Continued)

FOREIGN PATENT DOCUMENTS

| | | |
|---|---|---|
| EP | 0540266 A1 | 5/1993 |
| WO | WO 93/01861 A1 | 2/1993 |

(Continued)

OTHER PUBLICATIONS

International Search Report and Written Opinion for PCT Application No. PCT/US2013/074761, dated Apr. 3, 2014.

(Continued)

*Primary Examiner* — Brian T Gedeon
*Assistant Examiner* — Ankit D Tejani
(74) *Attorney, Agent, or Firm* — Patterson Thuente Pederson, P.A.

(57) ABSTRACT

Automated treatment of arrhythmia utilizing an electrotherapy device. Time-coordinated applications of medium-voltage therapy (MVT) followed by high-voltage therapy (HVT) include a first MVT waveform to a first target region and a second MVT waveform to a second target region, such that the HVT is synchronized relative to a first compression cycle corresponding to activation of the first target region, and to a second compression cycle corresponding to activation of the second target region resulting from the administration of the MVT.

19 Claims, 13 Drawing Sheets

(56) References Cited

U.S. PATENT DOCUMENTS

| | | |
|---|---|---|
| 4,146,029 A | 3/1979 | Ellinwood, Jr. |
| 4,181,133 A | 1/1980 | Kolenik et al. |
| 4,222,386 A | 9/1980 | Smolnikov et al. |
| 4,280,502 A | 7/1981 | Baker, Jr. et al. |
| 4,301,804 A | 11/1981 | Thompson et al. |
| 4,349,030 A | 9/1982 | Belgard et al. |
| 4,390,021 A | 6/1983 | Spurrell et al. |
| 4,398,536 A | 8/1983 | Nappholz et al. |
| 4,407,288 A | 10/1983 | Langer et al. |
| 4,408,606 A | 10/1983 | Spurrell et al. |
| 4,463,760 A | 8/1984 | Elmqvist |
| 4,488,553 A | 12/1984 | Nappholz et al. |
| 4,488,554 A | 12/1984 | Nappholz et al. |
| 4,552,561 A | 11/1985 | Eckenhoff et al. |
| 4,559,946 A | 12/1985 | Mower |
| 4,572,191 A | 2/1986 | Mirowski et al. |
| 4,623,248 A | 11/1986 | Sperinde |
| 4,686,988 A | 8/1987 | Sholder |
| 4,693,253 A | 9/1987 | Adams |
| 4,774,950 A | 10/1988 | Cohen |
| 4,823,800 A | 4/1989 | Compos |
| 4,830,006 A | 5/1989 | Haluska et al. |
| 4,945,909 A | 8/1990 | Fearnot et al. |
| 4,969,873 A | 11/1990 | Steinbach et al. |
| 4,986,270 A | 1/1991 | Cohen |
| 4,996,984 A | 3/1991 | Sweeney |
| 4,998,975 A | 3/1991 | Cohen et al. |
| 5,018,522 A | 5/1991 | Mehra |
| 5,041,107 A | 8/1991 | Heil, Jr. |
| 5,042,497 A | 8/1991 | Shapland |
| 5,087,243 A | 2/1992 | Avitall |
| 5,098,442 A | 3/1992 | Grandjean |
| 5,184,616 A | 2/1993 | Weiss |
| 5,193,535 A | 3/1993 | Bardy et al. |
| 5,193,537 A | 3/1993 | Freeman |
| 5,207,219 A | 5/1993 | Adams et al. |
| 5,220,917 A | 6/1993 | Cammilli et al. |
| 5,222,480 A | 6/1993 | Couche et al. |
| 5,230,336 A | 7/1993 | Fain et al. |
| 5,251,624 A | 10/1993 | Bocek et al. |
| 5,265,600 A | 11/1993 | Adams et al. |
| 5,282,836 A | 2/1994 | Kreyenhagen et al. |
| 5,282,837 A | 2/1994 | Adams et al. |
| 5,305,745 A | 4/1994 | Zacouto |
| 5,314,319 A | 5/1994 | Nilsson et al. |
| 5,314,448 A | 5/1994 | Kroll et al. |
| 5,330,505 A | 7/1994 | Cohen |
| 5,330,506 A | 7/1994 | Alferness et al. |
| 5,330,509 A | 7/1994 | Kroll et al. |
| 5,336,245 A | 8/1994 | Adams et al. |
| 5,350,402 A | 9/1994 | Infinger et al. |
| 5,376,103 A | 12/1994 | Anderson et al. |
| 5,391,185 A | 2/1995 | Kroll |
| 5,391,186 A | 2/1995 | Kroll et al. |
| 5,411,524 A | 5/1995 | Rahul |
| 5,431,687 A | 7/1995 | Kroll |
| 5,431,688 A | 7/1995 | Freeman |
| 5,464,434 A | 11/1995 | Alt |
| 5,470,341 A | 11/1995 | Kuehn et al. |
| 5,499,971 A | 3/1996 | Shapland et al. |
| 5,527,344 A | 6/1996 | Arzbaecher et al. |
| 5,601,611 A | 2/1997 | Fayram et al. |
| 5,607,385 A | 3/1997 | Francischelli et al. |
| 5,607,454 A | 3/1997 | Cameron et al. |
| 5,632,716 A | 5/1997 | Bui et al. |
| 5,658,237 A | 8/1997 | Francischelli |
| 5,662,689 A | 9/1997 | Elsberry et al. |
| 5,700,281 A | 12/1997 | Brewer et al. |
| 5,716,378 A | 2/1998 | Minten |
| 5,716,379 A | 2/1998 | Bourgeois et al. |
| 5,735,876 A | 4/1998 | Kroll et al. |
| 5,782,883 A | 7/1998 | Kroll et al. |
| 5,824,029 A | 10/1998 | Weijand et al. |
| 5,871,510 A | 2/1999 | Kroll et al. |
| 5,913,879 A | 6/1999 | Ferek-Petric et al. |
| 5,925,066 A | 7/1999 | Kroll et al. |
| 5,978,703 A | 11/1999 | Kroll et al. |
| 6,167,306 A | 12/2000 | Kroll et al. |
| 6,171,252 B1 | 1/2001 | Roberts |
| 6,185,457 B1 | 2/2001 | Kroll et al. |
| 6,230,056 B1 | 5/2001 | Kroll |
| 6,263,241 B1 | 7/2001 | Rosborough et al. |
| 6,298,267 B1 | 10/2001 | Rosborough et al. |
| 6,314,319 B1 | 11/2001 | Kroll et al. |
| 6,351,670 B1 | 2/2002 | Kroll |
| 6,398,744 B2 | 6/2002 | Bystrom et al. |
| 6,438,419 B1 | 8/2002 | Callaway et al. |
| 6,556,865 B2 | 4/2003 | Walcott et al. |
| 6,560,484 B1 | 5/2003 | Kroll et al. |
| 6,567,697 B1 | 5/2003 | Kroll et al. |
| 6,577,102 B1 | 6/2003 | Vaisnys et al. |
| 6,760,621 B2 | 7/2004 | Walcott et al. |
| 6,853,859 B1 | 2/2005 | Kroll et al. |
| 6,982,073 B2 | 1/2006 | Sabacky et al. |
| 7,011,637 B2 | 3/2006 | Sherman et al. |
| 7,035,684 B2 | 4/2006 | Lee |
| 7,383,085 B2 | 6/2008 | Olson |
| 7,488,293 B2 | 2/2009 | Marcovecchio et al. |
| 7,706,864 B2 | 4/2010 | Kroll et al. |
| 7,787,942 B2 | 8/2010 | Chinchoy et al. |
| 7,809,438 B2 | 10/2010 | Echt et al. |
| 7,957,799 B2 | 6/2011 | Sullivan et al. |
| 8,064,995 B1 | 11/2011 | Dupelle et al. |
| 8,121,681 B2 | 2/2012 | Hampton et al. |
| 8,160,703 B2 | 4/2012 | Stickney et al. |
| 8,165,662 B2 | 4/2012 | Cinbis et al. |
| 8,165,673 B2 | 4/2012 | Sherman et al. |
| 8,401,637 B2 | 3/2013 | Kroll et al. |
| 8,483,822 B1 | 7/2013 | Gilman et al. |
| 8,718,759 B2 | 5/2014 | Kroll |
| 8,750,990 B1 | 6/2014 | Gilman et al. |
| 8,805,495 B2 | 8/2014 | Gilman et al. |
| 8,868,178 B2 | 10/2014 | Gilman et al. |
| 9,061,164 B2 | 6/2015 | Gilman et al. |
| 9,144,684 B2 | 9/2015 | Gilman et al. |
| 2002/0156503 A1 | 10/2002 | Powers et al. |
| 2002/0161407 A1 | 10/2002 | Walcott et al. |
| 2004/0039313 A1 | 2/2004 | Sherman et al. |
| 2004/0044373 A1 | 3/2004 | Kroll et al. |
| 2004/0220628 A1 | 11/2004 | Wagner |
| 2005/0197676 A1 | 9/2005 | Kroll et al. |
| 2006/0142809 A1* | 6/2006 | Kroll ................ A61N 1/39 607/5 |
| 2007/0299473 A1 | 12/2007 | Matos |
| 2009/0149903 A1 | 6/2009 | Freeman |
| 2009/0177127 A1 | 7/2009 | Sherman et al. |
| 2012/0035675 A1 | 2/2012 | Walker et al. |
| 2013/0035735 A1 | 2/2013 | Kroll |
| 2014/0005734 A1 | 1/2014 | Gilman et al. |
| 2014/0236248 A1 | 8/2014 | Gilman et al. |
| 2014/0296930 A1 | 10/2014 | Kroll |
| 2014/0336718 A1 | 11/2014 | Gilman et al. |

FOREIGN PATENT DOCUMENTS

| | | |
|---|---|---|
| WO | WO 93/06866 A2 | 4/1993 |
| WO | WO 93/19809 A1 | 10/1993 |
| WO | WO 97/15351 A1 | 5/1997 |
| WO | WO 99/03534 A1 | 1/1999 |

OTHER PUBLICATIONS

International Search Report and Written Opinion for International PCT/US2012/049765, dated Dec. 3, 2012.
EP Application No. 05852106.3, Search Report dated Oct. 28, 2008, 1 pages.
EP Application No. 12820255, Search Report dated May 3, 2015.
Gilman et al., "Applying the Principles of Functional Stimulation to Electrical CPR". 2008.
Gilman et al., "Electrically Induced Chest Constrictions Produce Ventilation As Well As Cardiac Output", 2 pages, Jan. 2008.
Ristagno et al., "Transthoracic Application of Medium Voltage Therapy Maintains Forward Blood Flow During Cardiac Arrest", 2 pages, 2008.

(56) References Cited

OTHER PUBLICATIONS

Gilman, et al., Medium Voltage Therapy for Preventing and Treating Asystole and PEA and ICDs. 31st Annual International Conference, 3 pages, Sep. 2009.
Wang et al, "Coronary Blood Flow Produced by Muscle Contractions Induced by Intracardiac Electrical CPR during Ventricular Fibrillation", pp. S223-S227, Mar. 2009. vol. 32.
Wang et al, Transthoracic Application of Electrical Cardiopulmonary Resuscitation for Treatment of Cardiac Arrest. Crit Care Med. 2008, vol. 36, No. 11, 9 pages.
Koster, Limited 'hands-off' periods during resuscitation. 2003. pp. 275-276.
Snyder, "Wide variation in cardiopulmonary resuscitation interruption intervals among commercially available automated external defibrillators may affect survival despite high defibrillation efficacy", 2004. vol. 32, No. 9. pp. S421-S424.
Aufderheide TP, et al., "Death by hyperventilation: A common and life threatening problem during cardiopulmonary resuscitation." Wolf Creek VII, Ranch Mirage, CA Jun. 13-16, 2003.
Berg, RA et al., "Precountershock cardiopulmonary resuscitation improves ventricular fibrillation median frequency and myocardial readiness for successful defibrillation from prolonged ventricular fibrillation: a randomized, controlled swine study." Dec. 2002. vol. 40, Issue 6.
Cobb LA, et al., "Influence of cardiopulmonary resuscitation prior to defibrillation in patients with out-of-hospital ventricular fibrillation." JAMA Apr. 7, 1999; 281(13): 1182-8.
Eftestol T, et al., "Effects of interrupting precordial compressions on the calculated probability of defibrillation success during out-of-hospital cardiac arrest," Circulation May 14, 2002; 105(19): 2270-3.
Mr. Fell's Electrical Machine described, Gentleman's Magazine, Apr. 2, 1792.
Gilman, Byron et al., "Intracardiac Stimulation Produces Blood Flow During Ventricular Fibrillation," Cardiostim, Jun. 2008, 1 page.
Gilman, Byron et al., "Medium Voltage Therapy Produces Blood Flow for Prolonged Duration after Brief VF," HRS (Heart Rhythm Society), May 2008, 2 pages.
Idris AH, et al., "Effect of ventilation on resuscitation in an animal model of cardiac arrest," Circulation Dec. 1994; 90(6): 3063-9.
KenKnight, Bruce H., et al. "Regional Capture of Fibrillating Ventricular Myocardium: Evidence of an Excitable Gap." Circulation Research, vol. 77, No. 4, Oct. 1995.
Gilman, Byron et al., "Electrically Induced Chest Constrictions Produce Blood Flow During Ventricular Fibrillation Via Thoracic-Only Pump Mechanism," HRS, May 9, 2007, 2 pages.
Gilman, Byron et al., "Electrically Induced Chest Constrictions During Ventricular Fibrillation Produce Blood Flow," ACC, Mar. 26, 2007, Presentation #1019-195, 2 pages.
Abstract, MacDonald RD, et al., "Impact of prompt defibrillation on cardiac arrest at a major international airport," Prehosp Emerg Care 2002; 6: 1-5.
Abstract, Menegazzi, JJ et al., "Immediate defibrillation versus interventions first in a swine model of prolonged ventricular fibrillation," Resuscitation Nov. 2003; 59(2): 261-70.
Menegazzi, JJ et al., "Ventricular fibrillation scaling exponent can guide timing of defibrillation and other therapies," Circulation Feb. 24, 2004; 109(7): 926-31.
Murdock et al., "Augmentation of Cardiac Output by External Cardiac Pacing: Pacemaker-Induced CPR," Pacing and Clinical Electrophysiology, Jan. 1986, vol. 9, No. 1, Part 1, pp. 1-154.
Niemann, JT et al., "Immediate countershock versus cardiopulmonary resuscitation before countershock in a 5-minute swine model of ventricular fibrillation arrest." Ann Emerg Med Dec. 2000; 36(6): 543-6.
Paradis, NA, et al., "Coronary perfusion pressure and the return of spontaneous circulation in human cardiopulmonary resuscitation," J Am Med Assoc 1990;.263: 1106-13.
Rosborough JP et al., "Electrical therapy for post defibrillatory pulseless electrical activity." PACE 2000 (NASPE abstracts) p. 591.

Abstract, Sherman, LD, et al., "Ventricular fibrillation exhibits dynamical properties and self-similarity," Resuscitation 2000; 47: 163-73.
Abstract, Steen, S et al., "The critical importance of minimal delay between chest compressions and subsequent defibrillation: a haemodynamic explanation." Resuscitation Sep. 2003; 58(3): 249-58.
Abstract, Stotz M, et al., "EMS defibrillation-first policy may not improve outcome in out-of-hospital cardiac arrest," Resuscitation 2003; 58: 277-82.
Valenzuela, TD, et al., "Outcomes of rapid defibrillation by security officers after cardiac arrests in casinos." N Engl J Med 2000; 343: 1206-9.
Van Alem AP, et al., "Interruption of cardiopulmonary resuscitation with the use of the automated external defibrillator in out-of-hospital cardiac arrest," Ann.Emerg Med Oct. 2003; 42(4): 449-57.
Walcott GP et al., "Effects of burst stimulation during ventricular fibrillation on cardiac function after defibrillation." Am J Physiol Heart Circ Physiol Aug. 2003; 285(2): H766-74.
Wang, HF, et al., "Effects of biphasic vs. monophasic defibrillation on the scaling exponent in a swine model of prolonged ventricular fibrillation," Acad. Emerg Med 2001; 8: 771-780.
Wang, Hao MD et al., "Electrically Induced Chest Constrictions Produce Ventilation as Well as Cardiac Output," NAEMSP (National Association of Emergency Medical Service Physicians), Jan. 2008, 3 pages.
Wang, Hao MD et al., "Transthoracic Application of Medium Voltage Therapy for Treatment of Cardiac Arrest," AHA, Nov. 2007, 2 pages.
Abstract, Wik, L et al., "Delaying defibrillation to give basic cardiopulmonary resuscitation to patients with out-of-hospital ventricular fibrillation: a randomized trial," JAMA Mar. 19, 2003; 289(11): 1389-95.
Abstract, Xie, J, et al., "Spontaneous gasping generates cardiac output during cardiac arrest," Crit Care Med Jan. 2004 : 32(1): 238-40.
Aufderheide, Tom P. M.D., "Pacemakers and Electrical Therapy During Advanced Cardiac Life Support," Respiratory Care Apr. 1995 vol. 40. No. 4.
Bleske, et al., "Comparison of adrenergic agonists for the treatment of ventricular fibrillation and pulseless electrical activity," Resuscitation 28, pp. 239-251, Aug. 1994.
DeBehnke, Daniel, "Resuscitation time limits in experimental pulseless electrical activity cardiac arrest using cardiopulmonary bypass," Resuscitation 27, pp. 221-229, Feb. 28, 1994.
Schuder, J. C., et al., "Transthoracic Ventricular Defibrillation in the Dog With Unidirectional Rectangular Double Pulses," Cardiovascular Research, 4, 1970.
Wik, L, et al., "Rediscovery of the importance of compressions to improve outcome," Resuscitation 2003; 58: 267-269.
Love et al., Recommendations for Extraction of Chronically Implanted Transvenous Pacing and Defibrillator Leads: Indications, Facilities, Training. Apr. 2000. vol. 23. No. 4. Part 1. pp. 421-552.
Geddes, L.A., et al., "Electrically Produced Artificial Ventilation," Perspective and Progress vol. 22, No. 5, pp. 263-271 (1988).
Geddes, L.A., et al., "Ventricular Defibrillation With Single and Twin Pulses of Half-sinusoidal Current," Journal of Applied Physiology, vol. 34, No. 1, Jan. 1973.
Weng et al., A Novel Electrical Therapy for Postshock PEA in a Porcine Model and abstract, 2011.
Glenn, William W.L. et al., "Twenty Years of Experience in Phrenic Nerve Stimulation to Pace the Diaphragm," PACE, vol. 9, Nov.-Dec. 1986, Part I.
KenKnight, B.H., et al., "Regional Capture of Fibrillating Right Ventricular Myocardium Evidence of an Excitable Gap in VF Using High Resolution Cardiac Mapping," J.A.C.C., Feb. 1994, p. 283A.
Kirchhof, C., et al., "Regional Entrainment of Atrial Fibrillation Studied by High-Resolution Mapping in Open-Chest Dogs," Circulation, vol. 88, No. 2, Aug. 1993.
Kugelberg, J., "Ventricular Defibrillation—A New Aspect," Acta Chirurgica Scandinavica, Suppl. No. 372, 1967.
Kugelberg, J. E., "Ventricular Defibrillation With Double Square Pulse," Medical & Biological Engineering, vol. 6, 1968.

(56) References Cited

OTHER PUBLICATIONS

Laghi, Franco, et al., "Comparison of Magnetic and Electrical Phrenic Nerve Stimulation in Assessment of Diaphragmatic Contractility," Appl. Physiol. 80(5): 1731-1742 1996.

Leng, Charles T. M.D., et al., "Electrical Induction of Ventricular Fibrillation for Resuscitation From Postcountershock Pulseless and Asystolic Cardiac Arrests," Circulation pp. 723-728 (Aug. 7, 2001).

Murakawa, Yuji, et al. "The Effect of an Unsuccessful Subthreshold Shock on the Energy Requirement for the Subsequent Defibrillation." American Heart Journal, May 1989.

Quinn, et al., "Need for Sedation in a Patient Undergoing Active Compression—Decompression Cardiopulmonary Resuscitation," Academic Emergency Medicine, vol. 1, No. 5, pp. 463-467, Sep./Oct. 1994.

Resnekov, L., "Ventricular Defibrillation by Monophasic Trapezoidal-shaped Double-pulses of Low Electrical Energy," Cardiovascular Research, 2, 1968a.

Li et al., "The Optimal Phasic Relationship Between Synchronized Shock and Mechanical Chest Compressions," Elsevier, 724-729, Feb. 22, 2010.

Application and File History for U.S. Appl. No. 11/285,756, filed Nov. 22, 2005, now U.S. Pat. No. 8,401,637. Inventors: Kroll et al.

Application and File History for U.S. Appl. No. 12/830,251, filed Jul. 2, 2010, now U.S. Pat. No. 8,483,822. Inventors: Gilman et al.

Application and File History for U.S. Appl. No. 13/921,290, filed Jun. 19, 2013, now U.S. Pat. No. 8,805,495. Inventors: Gilman et al.

Application and File History for U.S. Appl. No. 14/337,700, filed Jul. 22, 2014, now U.S. Pat. No. 9,144,684. Inventors: Gilman et al.

Application and File History for U.S. Appl. No. 14/867,804, filed Sep. 28, 2015. Inventors: Gilman et al.

Application and File History for U.S. Appl. No. 13/567,699, filed Aug. 6, 2012, now U.S. Pat. No. 8,718,759. Inventor: Kroll.

Application and File History for U.S. Appl. No. 14/248,815, filed Apr. 9, 2014. Inventor: Kroll.

* cited by examiner

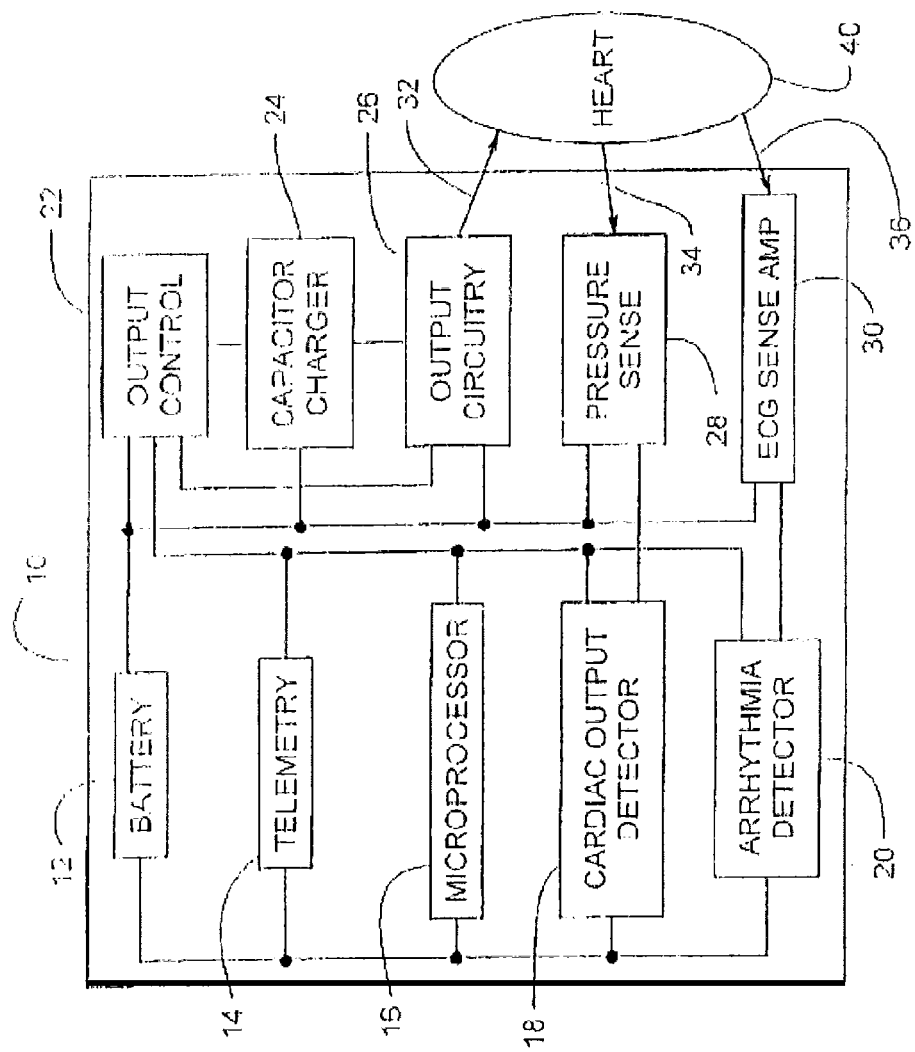

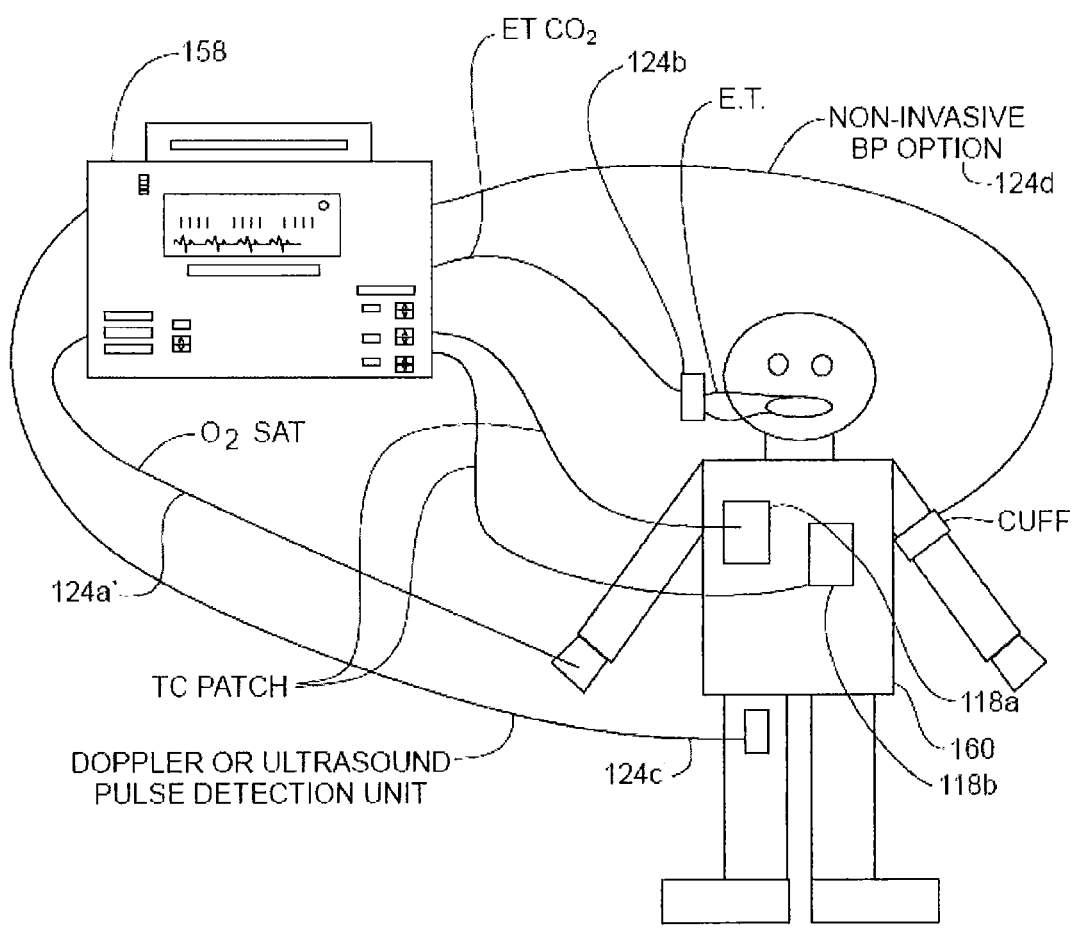

COORDINATED MEDIUM VOLTAGE THERAPY FOR IMPROVING EFFECTIVENESS OF DEFIBRILLATION THERAPY

CROSS-REFERENCE TO RELATED APPLICATIONS

This application is a continuation of application Ser. No. 14/259,892 filed Apr. 23, 2014, now issued as U.S. Pat. No. 9,061,164, which is a continuation of application Ser. No. 13/712,683 filed Dec. 12, 2012, now issued as U.S. Pat. No. 8,750,990, the disclosures of which are hereby incorporated by reference.

FIELD OF THE INVENTION

The invention relates generally to electrical treatment for individuals experiencing cardiac arrest and, more particularly, to implantable or external treatment apparatus and associated methods of operation thereof, for improving the effectiveness of defibrillation treatment utilizing coordinated administration of medium voltage therapy (MVT).

BACKGROUND OF THE INVENTION

Cardiac arrest is a significant public health problem cutting across age, race, and gender. A positive impact on cardiac arrest survival has been demonstrated with the substantial reduction in time to defibrillation provided by the widespread deployment of automated external defibrillators (AEDs), and the use of implantable cardioverter defibrillators (ICDs) and implantable pulse generators (IPGs). Examples of AEDs are described in U.S. Pat. Nos. 5,607,454, 5,700,281 and 6,577,102; examples of ICDs are described in U.S. Pat. Nos. 5,391,186, 7,383,085, and 4,407,288, and examples of IPGs are described in U.S. Pat. Nos. 4,463,760, 3,978,865, and 4,301,804, the disclosures of which are incorporated by reference herein.

Optimal resuscitation therapy for out of hospital (OOH) cardiac arrest is the subject of substantial ongoing research. Research has been clear in demonstrating that the timing of resuscitation is of critical importance. For example, there is less than a 10% chance of recovery just ten minutes after the onset of ventricular fibrillation (VF). This knowledge led to the recent widespread deployment of AEDs, primarily in public areas with a high population concentration such as airports and shopping malls. A positive impact on cardiac arrest survival has been demonstrated due to the substantial reduction in time to defibrillation as a result of more available access to AEDs. In addition, for those patients identified as being at particularly high risk, an implantable cardioverter-defibrillator is often implanted in order to address episodes of cardiac arrest without the involvement of a rescuer.

In the case of VF, performing CPR-type chest compressions before defibrillation or between successive defibrillation shocks and minimizing the time to defibrillation shock following the cessation of the CPR chest compressions is important in facilitating effective recovery especially in cases of long duration VF. It is generally believed that perfusion of the myocardium achieved during CPR preconditions the heart for the defibrillating shock. Despite the importance of CPR, it is often not performed in the field for a variety of reasons.

MVT has also been recognized as a way of forcing some amount of cardiac output by electrically stimulating muscle tissue directly with stimuli that cause the heart or skeletal muscles to contract in a controlled cycle. See U.S. Pat. Nos. 5,735,876, 5,782,883 and 5,871,510. These patents describe implantable devices having combined defibrillation, and MVT capability for forcing cardiac output. U.S. Pat. No. 6,314,319 describes internal and external systems and associated methods of utilizing MVT to achieve a hemodynamic effect in the heart as part of an implantable cardioverter defibrillator (ICD) for purposes of achieving a smaller prophylactic device. The approach described in the '319 patent uses the MVT therapy to provide a smaller and less expensive implantable device that can maintain some cardiac output without necessarily providing defibrillation therapy.

Unlike a conventional defibrillator, which operates with the primary purpose of restoring a normal cardiac rhythm, or an IPG that operates to control the rate of an existing cardiac rhythm, MVT stimulation can be used to provide cardiac output, which in turn causes perfusion to the heart and brain, as well as other critical body tissues. By providing perfusion to the heart and other vital organs, MVT prolongs the life of the patient even while the patient continues experiencing the arrhythmia. Additionally, MVT improves the likelihood of successful defibrillation or of a spontaneous return of circulation. An AED equipped with MVT can provide consistent high quality chest compressions. In the case of an implanted ICD or IPG, back up chest compressions provided by MVT can, in one sense, be even more important than in an external, since in the case of the implantable device there may be no rescuer available to perform CPR when needed.

U.S. Patent Application Publication No. 2006/0142809, the disclosure of which is incorporated by reference herein, describes a technique and associated apparatus that combines defibrillation therapy with MVT into an external device having a capability to perform electrical CPR. Externally-applied MVT is proposed for stimulating skeletal and sympathetic muscles in addition to myocardial muscle tissue to effect chest compression and even ventilation in the patient. The '809 publication reflects the knowledge in the art that due to the inclusion of differing time constant components in an MVT waveform, the waveform can stimulate contraction of a variety of different types of muscles, e.g., myocardial, skeletal, sympathetic muscles, and the phrenic nerve. Varying and controlling the MVT waveform parameters, including variation of the musculature targeted by the waveform, is described as a way to maximize coronary perfusion pressure generated by application of MVT.

Separately, there have been developments in automated chest compression devices that apply mechanical pressure in repeated CPR-like cycles to a patient's chest area. These devices may incorporate defibrillation therapy as well, such as disclosed in U.S. Pat. No. 6,398,744. Although mechanical chest compression devices are useful in situations where sustained manual CPR is difficult or tiring for rescuers, such as in lengthy ambulance trips or airlifts, for example, these devices include a belt that must be positioned around a patient's chest, making them generally unsuitable for use by layperson rescuers. There is also no implantable analogous device that could apply mechanical chest compressions.

More recently, a mechanical chest compression device has been used to study the effects of delivering defibrillation therapy at various points in the chest compression cycle. U.S. Pub. No. 2009/0149903 discloses the results of animal research in which the mechanical chest compression cycle of a porcine model was measured directly using a load cell force transducer, the output of which was used to control the time of application of the defibrillation energy. The empirical results of this work suggest that application of the defibrillation therapy at the end upstroke phase of the compression cycle produced an increased success rate of converting the ventricular fibrillation.

It would be desirable to apply some of these chest compression cycle-defibrillation synchronization principles learned from mechanical chest compression technology to devices utilizing MVT to take advantage of the ease of use of AED devices requiring only the placement of electrodes, plus the ability to implement compression cycle-defibrillation synchronization in implantable devices. Previously, it has been proposed to time a defibrillation shock after a skeletal muscle stimulating pre-shock waveform for an implanted subcutaneous device, as disclosed in U.S. Pub. No. 2004/00220628. This approach attempts to compress the thorax to reduce conduction path length for the subsequent defibrillation shock, thereby reducing the defibrillation shock impedance and concentrating the defibrillation current to the heart.

Synchronizing electrically-stimulated chest or heart compressions with defibrillation therapy presents its own set of challenges. Although the defibrillation pulses can be precisely timed relative to the start or cessation of the muscle stimulation by triggering the discharge of appropriate waveforms and energy at the appropriate times, synchronizing the defibrillation pulses to the chest compressions themselves is not so straight-forward to control. For instance, each individual patient has a particular size, chest cavity structure, lung volume, skeletal muscle mass, muscle tone, heart volume and mass, etc. These all factor into the characteristics of the compression cycle that can be produced by applying MVT, and vary patient-to-patient. Likewise, the particular patient's disease state or symptoms thereof, such as cardiomegaly, i.e., enlarged heart, for example, can affect the timing and quality of the compression cycle induced by MVT administration. Moreover, electrical muscle stimulation approaches cannot directly measure the compression cycle using the type of load cell sensor disclosed in the 2009/0149903 publication.

The 2004/00220628 publication recognizes some of these challenges and proposes that the time delay between the pre-shock waveform and the defibrillation shock be varied patient-to-patient or shock-to-shock. However, this reference does not address how the time delay is to be varied, or what the basis for varying the time delay should be. Moreover, it is not apparent from the art whether the seemingly contradictory teachings of the 2004/00220628 publication emphasizing applying the defibrillation shock at the point where the chest is most compressed, can be reconciled with the findings of U.S. Pub. No. 2009/014990 suggesting the optimal point of defibrillation shock delivery should be when the chest has rebounded after a chest compression.

Optimal arrhythmia treatment continues to be a subject of ongoing research and development. In spite of the substantial progress in the research to understand the underlying biological mechanisms in electrical conversion of arrhythmias, a complete understanding (beyond here hypotheses) of the effects of all of the associated parameters, such as the effect of chest compressions, has been elusive. There remains a need for further improvement of treatment apparatus and associated processes to increase the effectiveness of these life-saving therapies.

SUMMARY OF THE INVENTION

One aspect of the invention is directed to automated treatment of arrhythmia utilizing an electrotherapy device. Time-coordinated applications of medium-voltage therapy (MVT) followed by high-voltage therapy (HVT) are administered as a time-coordinated sequence. The sequence includes a first MVT waveform to a first target region and a second MVT waveform to a second target region, such that the HVT is synchronized relative to a first compression cycle corresponding to activation of the first target region, and to a second compression cycle corresponding to activation of the second target region resulting from the administration of the MVT.

In a related aspect, an electrotherapy device for treating arrhythmia in a patient includes a patient interface, patient monitoring circuitry, electrotherapy circuitry, and a controller circuit.

The patient interface includes a plurality of electrodes, each having a surface that facilitates electrical contact with the patient. The electrotherapy circuitry is operatively coupled to the patient interface and includes a medium voltage therapy (MVT) circuit operatively coupled to the patient interface and constructed to administer MVT via the patient interface to each of a plurality of target regions of the patient. The MVT has an insufficient energy level to shock the heart into a reset state, but having an energy level and a variable waveform that causes musculature in each corresponding target region to be (a) electrically activated into a contracted state, (b) electrically maintained in the contracted state for a compression duration, and (c) thereafter allowed to relax, thereby achieving a forced compression and release of that target region. The plurality of target regions includes a first target region having primarily skeletal musculature, and a second target region having primarily myocardial musculature. A high voltage therapy (HVT) circuit is operatively coupled to the patient interface and constructed to supply the HVT via the patient interface. The HVT is of an energy level sufficient to shock the heart into a reset state.

The patient monitoring circuitry includes an arrhythmia monitoring circuit operatively coupled to the patient interface and configured to measure indicia of an arrhythmia treatable by the HVT.

The controller circuit is operatively coupled to the patient monitoring circuitry and the electrotherapy circuitry, and includes MVT administration logic configured to cause the electrotherapy circuitry to administer the MVT as a series of repeated, time-coordinated, applications of MVT waveforms to the first and the second target regions, respectively, in response to a detection of a presence of an arrhythmia treatable by the HVT based on an output of the patient monitoring circuitry. Also, the controller includes HVT administration logic configured to cause the electrotherapy circuitry to administer the HVT in response to the detection of the presence of the arrhythmia treatable by the HVT, and in time-coordinated response to a sequence of the time-coordinated applications of the MVT that includes a first MVT waveform to the first target region and a second MVT waveform to the second target region, such that the HVT is synchronized relative to (a) a first compression cycle corresponding to activation of the first target region, and (b) a second compression cycle corresponding to activation of the second target region, resulting from the administration of the MVT.

A number of advantages will become apparent from the following Detailed Description of the Preferred Embodiments.

BRIEF DESCRIPTION OF THE DRAWINGS

The invention may be more completely understood in consideration of the following detailed description of various embodiments of the invention in connection with the accompanying drawings, in which:

FIG. 1 is a diagram illustrating the sub-systems of an implantable device enabled with medium voltage therapy (MVT) facilities, according to one embodiment.

FIG. 3C is a diagram illustrating various examples of electrodes and sensors of the patient interface of the device of FIG. 3A.

Figure 2A:
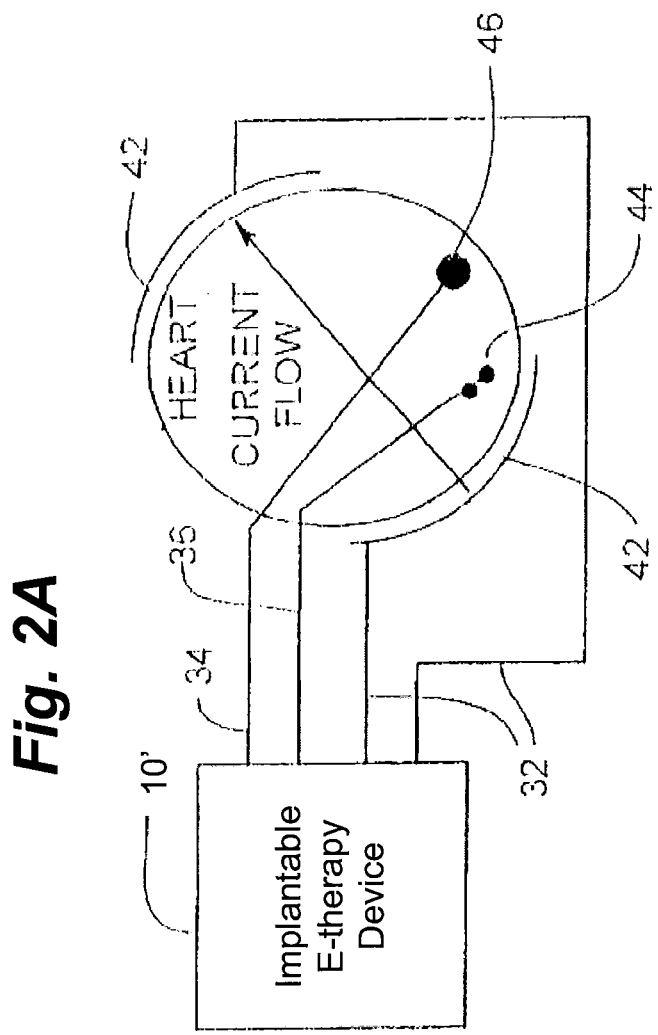
FIGS. 2A-2C illustrate various examples of electrode arrangements for implantable MVT devices such as the device of FIG. 1 according to various embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

FIG. 1 is a block diagram illustrating an implantable electrotherapy device 10 constructed in accordance with one aspect of the invention. The device circuitry is electrically coupled with regions of the patient's upper body 40 via a series of leads—output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 which determines if an arrhythmia is present. The arrhythmia detector 20 may be one of several types well known to those skilled in the art and is preferably able to distinguish between different types of arrhythmias. For example; fibrillation, tachycardia, asystole.

The exemplary circuit also contains a hemodynamic sensing section 28 which amplifies and conditions a signal from a one or more hemodynamic sensors such as, for example, a pressure sensor within the heart or artery, such as the pressure sensor described in U.S. Pat. No. 6,171,252, the disclosure of which is incorporated by reference herein. Another type of hemodynamic sensor that can be used in an implantable embodiment is a microphone and associated processing device for monitoring audible body sounds (much like an indwelling stethoscope) indicative of blood flow as described in U.S. Pat. No. 7,035,684, the disclosure of which is incorporated by reference herein. Yet another suitable hemodynamic sensing technique is one featuring an ultrasonic blood flow sensor, such as the Doppler pulse sensor described in U.S. Pat. No. 4,823,800, the disclosure of which is incorporated by reference herein. Still another hemodynamic sensing technique that may be employed is impedance plethysmography (tomography) in which a series of electrodes are placed to measure changing impedance in localized regions indicative of blood flow, a pulse, or movement of the cardiac wall such as described in U.S. Pat. No. 5,824,029, the disclosure of which is incorporated by reference herein. A further technique of measuring the hemodynamic output of the patient is with the use of a pulse oximeter such as the implantable one described in U.S. Pat. No. 4,623,248, the disclosure of which is incorporated by reference herein.

The output of the hemodynamic sense circuit 28 is fed to a cardiac output detection circuit 18 which analyzes the data and determines an estimate of the cardiac output. Data from the arrhythmia detector circuit 20 and the cardiac output detection circuit 18 is fed to the controller 16. The controller 16 determines if electrotherapy, such as defibrillation or MVT, is appropriate, and what electrotherapy parameters to apply at the present time. If defibrillation or MVT is indicated, the controller 16 prompts the output control 22 to charge a capacitor within the output circuit 26 via the capacitor charger 24. The output control 22 directs the output circuitry 26 to deliver the pulses to the patient's upper body regions 40 via the output leads 32. The controller 16 may communicate with external sources via a telemetry circuit 14 within the device 10. The power for the device 10 is supplied by an internal battery 12.

FIG. 2A is a diagram showing the connection of an implantable defibrillation device 10' according to one embodiment to the heart as one of the regions in the patient's upper body 40 in an epicardial patch configuration. In this thoracotomy configuration, current passes through an output lead pair 32 to electrode patches 42 which direct the current through the heart. A pressure sense lead 34 passes the signal from an optional pressure transducer 46 which lies in the heart. The ECG is monitored by sense electrodes 44 and passed to the device 10' by a lead 36. The area of the electrodes 42 is at least 0.5 cm². The size of the electrode is greater than that of a pacing lead, or between approximately 0.5 cm² and 20 cm² each.

Figure 2B:
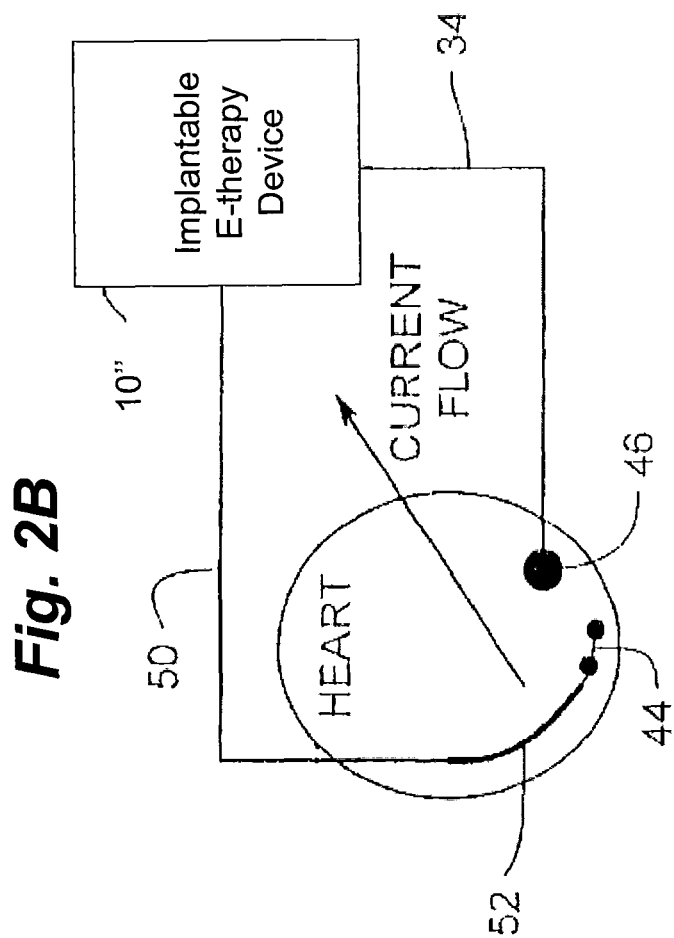

FIG. 2B illustrates an example of a non-thoracotomy arrangement according to one embodiment. In this system, the current passes from a coil electrode 52 in the heart to the housing of the MVT device 10". An endocardial lead 50 combines the ECG sensing lead and the pulse output lead. The ECG is monitored by sense electrodes 44 in the heart and passes through the endocardial lead 50. There is an optional pressure transducer 46 in the heart which passes a signal to the device 10" via optional lead 34.

Figure 2C:
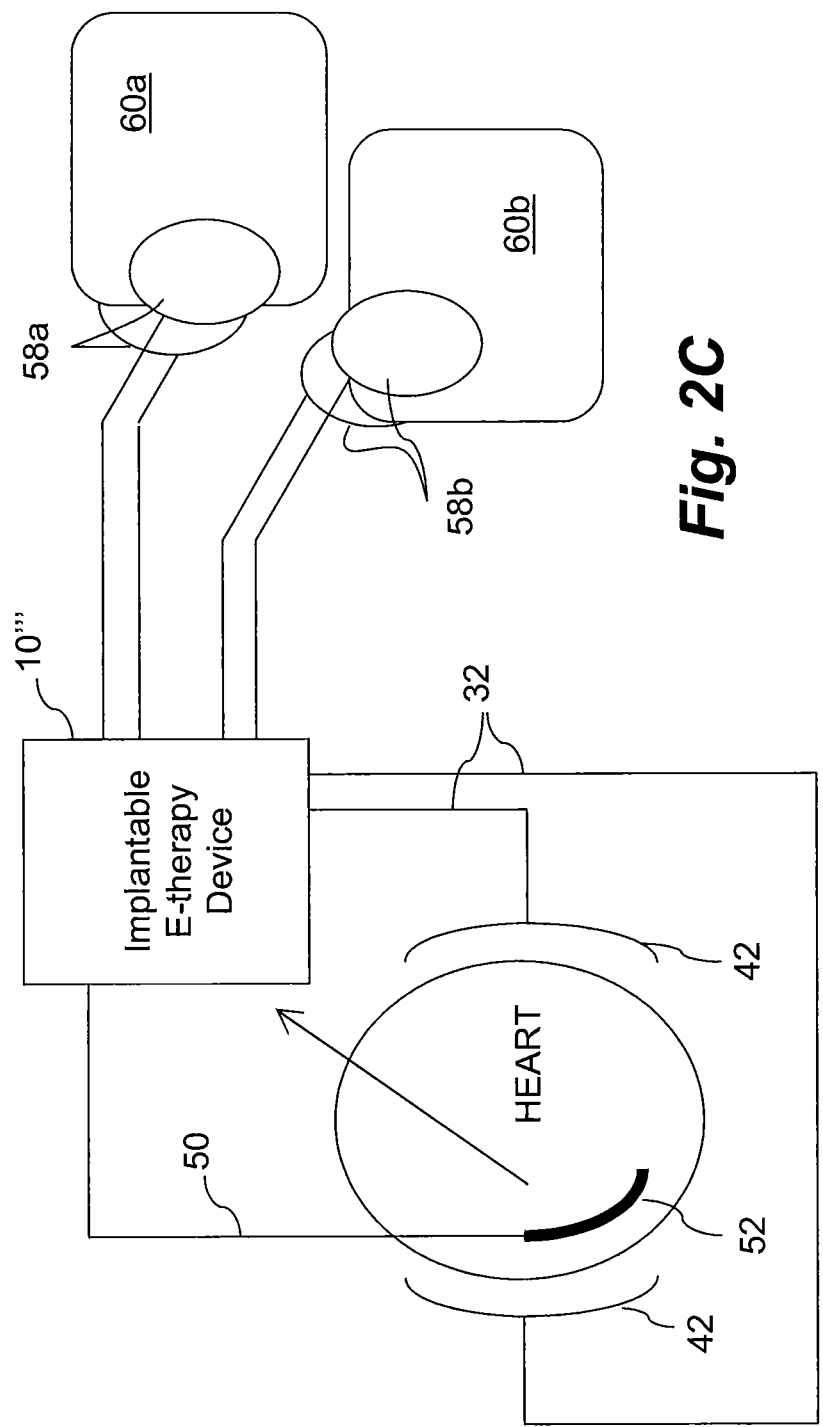

FIG. 2C illustrates an implantable electrotherapy device 10''' that supports a set of diverse electrode arrangements for selectively applying defibrillation, as well as MVT, to different areas of the patient. In addition to electrodes 42 and 52 discussed above in the thoracotomy and non-thoracotomy arrangements for directing the MVT through the myocardium, device 10''' further includes additional electrodes 58a and 58b for placement at specific locations in the patient's upper body, 60a and 60b, to direct MVT through non-cardiac muscles. Examples of locations 60a and 60b include (without limitation) locations for activating the pectoral muscles, intercostals muscles, the diaphragm (e.g., via stimulation of the phrenic nerve), and the abdominal muscles. The additional electrodes 58a and 58b, in various embodiments, have a variety of constructions and locations, including, for example, subcutaneous patch electrodes, one or more additional electronics/battery housings, intra-vascular leads, and the like. Placements include any suitable location such as, for example, subcutaneously at the base of the neck, in the azygos vein, in the cephalic vein, subcutaneously in the lower torso, and subcutaneously on one or both sides of the upper torso.

In a related embodiment, the additional one or more of electrodes 58a and 58b are used for hemodynamic measurements such as, for example, electrical impedance plethysmography or tomography. In one such embodiment, one of the additional electrodes 58a, for instance, is implanted high in the upper chest region or at the base of the neck, while another one of the additional electrodes, 59a, for instance, is implanted lower in the abdominal region. Even though electrode 58a and electrode 59a may not used as a cathode/anode pair for application of MVT (this would be the case where, for example, electrode 58a has a complementary electrode 58a placed elsewhere for applying MVT to region 60a, and where electrode 59a has a complementary electrode 59a placed elsewhere for applying MVT to region 60b), one of electrodes 58a and one of electrodes 59a can be operated as an anode/cathode pair with each other for purposes of impedance measurement to determine blood flow, using a suitable switching arrangement in the implantable MVT device 10'''.

In a related embodiment, an electrical impedance measurement is performed using frequency division or code division multiplexing relative to applied MVT therapy. Thus, the impedance measurement may be carried out while rejecting the interference caused by application of the MVT signals. This approach permits a hemodynamic impedance measurement to be performed without having to interrupt application of the MVT and without having to time the measurement to coincide with time periods between MVT pulse packets. Accordingly, in one embodiment, a real-time, continuous hemodynamic monitoring is performed while MVT is administered. The blood flow can thus be plotted as a function of time, and correlated to the parameters of the MVT being applied. This information can be displayed to an operator as a chart recording or displayed trace, and can be automatically stored and analyzed to ascertain MVT performance.

Figure 3A:
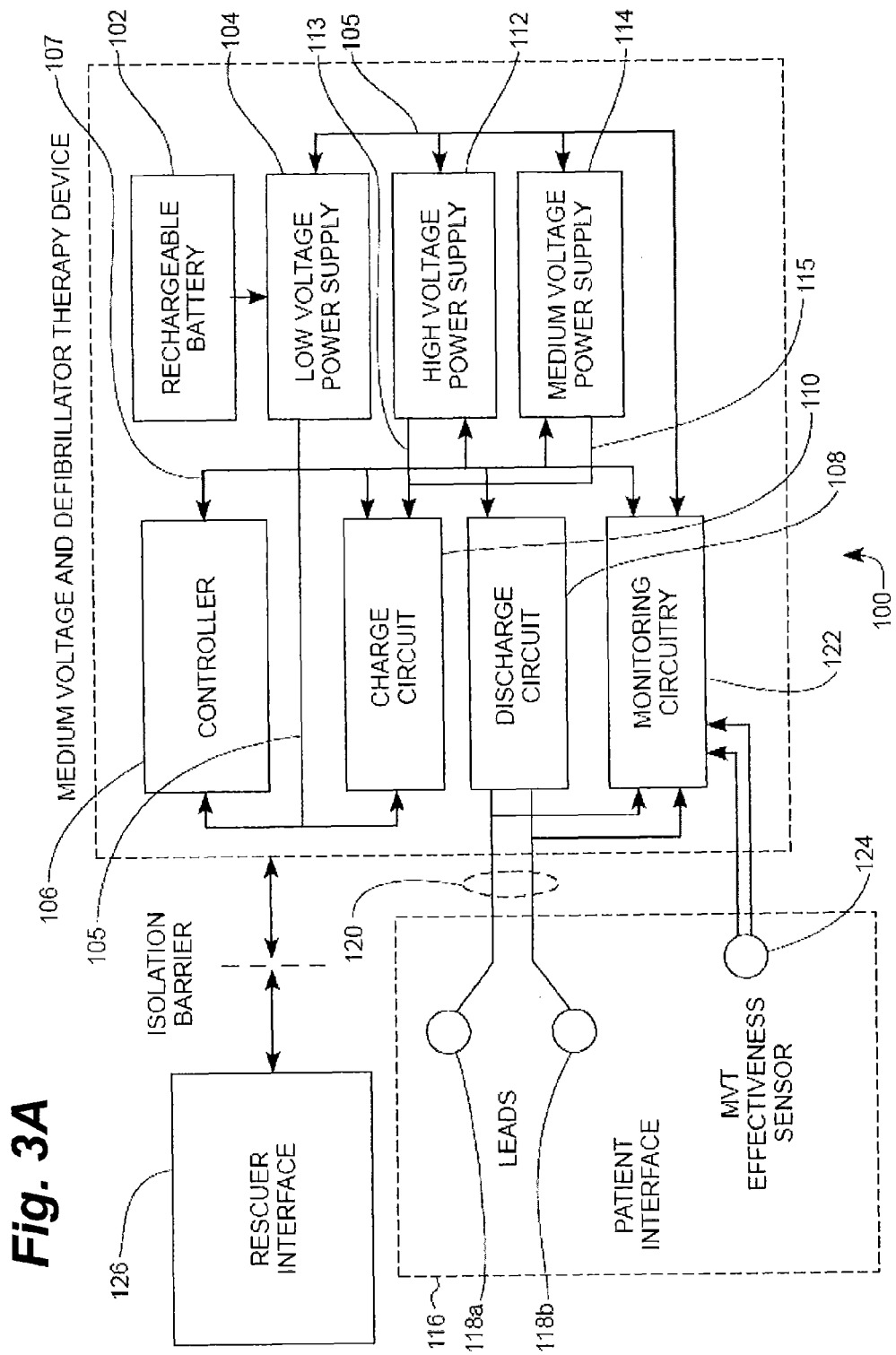
FIG. 3A is a diagram illustrating the sub-systems of an external device enabled with medium voltage therapy facilities, according to one embodiment.

FIG. 3A is a diagram illustrating an example AED 100 that utilizes MVT according to one embodiment. AED 100 can be a hand-portable instrument that is self-powered from an optionally-rechargeable battery 102. Battery 102 provides an energy source that can be converted and conditioned for powering the various circuitry of AED 100. A low voltage power supply 104 converts the battery power into one or more stabilized power supply outputs 105 for supplying the power to the subsystems of AED 100. The subsystems include a controller 106, for example a microprocessor that is programmed and interfaced with other subsystems to control most of the functionality of AED 100.

In the embodiments in which the controller 106 is implemented as a microprocessor or microcontroller, the microprocessor interface includes data and address busses, optional analog and/or digital inputs, and optional control inputs/outputs, collectively indicated at microprocessor interface 107. In one example embodiment, the microprocessor is programmed to control the sequence of the electrotherapy, as well as the output waveform parameters. The user input to the system can be in the form of simple pushbutton commands, or voice commands.

Example AED 100 includes a discharge circuit 108 for administering therapeutic stimuli to the patient. Discharge circuit 108 controls the release of therapeutic energy to achieve a desired stimulus having a particular waveform and energy. Charge circuit 110 energizes discharge circuit 108 to achieve the desired output stimulus. High voltage power supply 112 provides a sufficient energy source 113 to charge circuit 110 to enable charge circuit 110 and discharge circuit 108 to ultimately deliver one or more defibrillation pulses to an exterior surface of the patient. Typically, a voltage sufficient to achieve a therapeutic defibrillation stimulus from the exterior of a patient is in the range of 1 kV-3 kV.

In accordance with this embodiment, AED 100 also includes a medium voltage power supply 114. Medium voltage power supply 114 provides a medium voltage source 115 that enables charge circuit 110 and discharge circuit 108 to ultimately deliver one or more MVT signals to the exterior of the patient. In one embodiment, the medium voltage power supply is adapted to provide a regulated voltage in the range from 20-1000 V.

The defibrillation and MVT stimuli are administered to the patient via patient interface 116. In one embodiment, patient interface 116 includes electrodes 118a and 118b that are adhesively applied to the patient's chest area, typically with an electrically-conductive gel. Electrodes 118a and 118b are electrically coupled, such as by insulated copper wire leads 120, to discharge circuit 108. In one example embodiment, electrodes 118a and 118b can deliver the defibrillation stimuli and the MVT stimuli as well as obtain information about the patient's condition. For example, electrodes 118 can be used to monitor the patient's cardiac rhythm. Signals originating in the patient that are measured by electrodes 118 are fed to monitoring circuitry 122.

In one embodiment, electrodes 118a and 118b are part of compound electrode patches in which each patch (having a common substrate) has a plurality of individually-selectable electrodes. In this arrangement, device 100 is programmed to select certain ones of the individual electrodes on each compound patch to achieve a therapeutic purpose. One such purpose is to activate an individual electrode that is most optimally placed on the patient's body for the desired MVT or defibrillation therapy. This approach can be used to correct for the variability in placement of the electrode patches by unskilled rescuers or even skilled rescuers working under difficult circumstances in the field. Device 100 in this embodiment may include a switching arrangement, either electromechanical or electronic, or may communicate control information to an external switching arrangement, which may be incorporated into the compound patch. In a related embodiment, the ECG signal strength, as measured using various pairs of the individual electrodes of the compound patches, is used to determine the electrodes to be used for MVT and/or defibrillation administration. In another related embodiment, the hemodynamic measurement of the MVT effectiveness, as recorded for different electrode pairs, is used as a basis for switchably selecting the electrodes to be used for defibrillation. In yet another embodiment, certain electrodes are selected from among the plurality of electrodes on each compound patch to target specific regions to which MVT is to be applied.

In one embodiment, patient interface 116 includes an MVT effectiveness sensor 124 coupled to monitoring circuitry 122. MVT effectiveness sensor 124 can measure observable patient characteristics that are related to the patient's condition, in like fashion to the hemodynamic monitoring and determining arrangements described above for an implantable embodiment. Additional details about the MVT effectiveness monitoring are discussed below.

AED 100 also includes a rescuer interface 126 operatively coupled with controller 106. In one embodiment, rescuer interface 126 includes at least one pushbutton, and a display device for indicating at least the operational status of AED 100. In a related embodiment, rescuer interface includes a system for providing visual or audible prompting or instructions to the rescuer. In another embodiment, rescuer interface 126 includes a plurality of human-operable controls for adjusting the various AED operational parameters, and a display device that indicates measurements made by monitoring circuitry 122.

Figure 3B:
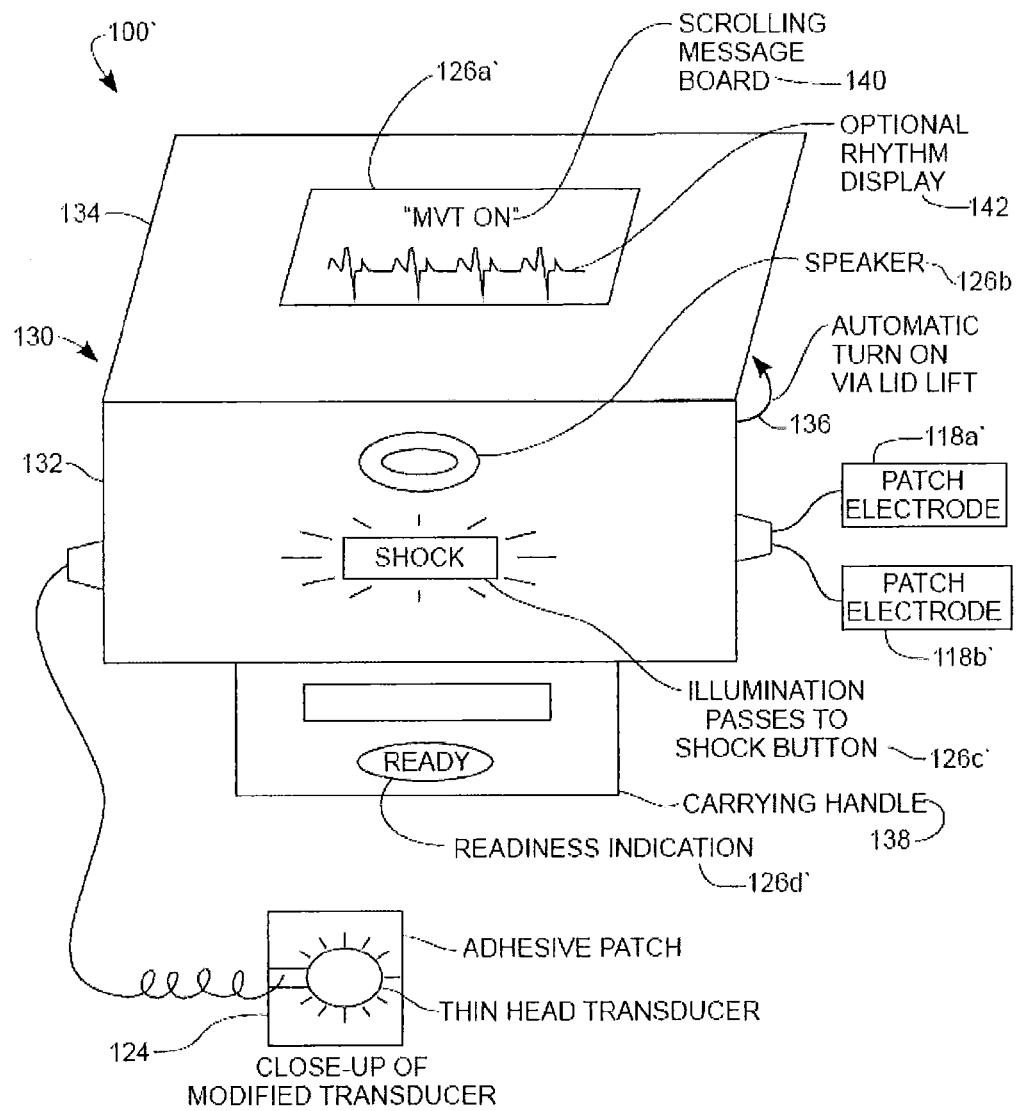
FIG. 3B is a diagram illustrating an exemplary operator interface of the device of FIG. 3A.

FIG. 3B is a diagram illustrating human interface portions of example AED 100' according to one embodiment. AED 100' is a physical implementation of AED 100 (FIG. 1A). AED 100' is housed in a lightweight portable housing 130 having a base portion 132 and a hinged lid 134 in an exemplary clam-shell arrangement as illustrated, where opening and closing of the lid turns the device on and off, as diagrammed at 136. Other embodiments do not have the base-cover arrangement, and instead have a housing consisting of a single enclosure, in which case the device has an on/off switch. The device's relatively small size and weight, and carrying handle 138 facilitate hand-portability of the device. Display 126a' may have a text only display 140 or may include a graphical display 142 that could, among other items, display an ECG waveform. The device also has a speaker 126b for voice prompting of the proper rescue sequence, a non-volatile readiness indicator 126d' that indicates whether or not the device is in working order, an optional "shock" button 126c' and receptacles for the patient electrodes 118a' and 118b' and an MVT effectiveness sensor 124'.

AED 100' includes two types of patient interface. First, electrodes 118a' and 118b' are adapted to be adhesively coupled to the patient's skin. In one embodiment, the adhesive consists of an electrically conductive gel. Electrodes 118a' and 118b' can be used to measure the patient's cardiac rhythm, and to apply MVT and defibrillation therapy to the patient. Second, MVT effectiveness sensor 124' includes a transducer adapted for measuring one or more vital signs of the patient.

FIG. 3C is a diagram of several possible patient 160 connections to an AED 158 according to one embodiment including: defibrillation/ECG electrodes 118a' and 118b', pulse oximeter 124a', ETCO2 sensor 124b', Doppler or ultrasound pulse sensor 124c', and blood pressure sensor 124d'. More generally, the MVT Effectiveness sensor can be a variant of any of the monitoring techniques discussed above, for instance, the pulse oximetry measurement for an external embodiment may be achieved using a fingertip pulse oximeter as the MVT effectiveness sensor 124. Other suitable techniques for monitoring a hemodynamic state of the patient may also be used. For instance, alternatively or in conjunction: a pulse oximeter, a sonic arterial pulse sensor, a gas sensor, or a blood pressure sensor. In another embodiment, the $O_2$ saturation sensor 124a', end tidal sensor 124b', and pulse detection unit 124c', are battery-powered and are adapted to communicate measurement data via wireless radio frequency link. For example, BLUETOOTH technology could be utilized to accomplish close-range wireless data communications.

In one example embodiment, arterial pulse activity measured from an exterior of the patient by way of pressure sensing, or by way of Doppler ultrasound technology. In one embodiment, the MVT effectiveness sensor includes a transthoracic impedance measuring arrangement that detects changes in the chest impedance with cardiac output. Referring again to FIG. 3B, in one embodiment, MVT effectiveness sensor 124' is integrated with an adhesive patch adapted to be attached to the patient's skin. In a related embodiment, the transducer portion of MVT effectiveness sensor 124' is implemented in a thin-or-thick-film semiconductor technology. Examples of suitable sites for arterial pulse sensing include the patient's aorta, femoral arteries, carotid arteries, and brachial arteries. Other accessible arteries may also be suitable. In one example embodiment of AED 100', the measurement collected via MVT effectiveness sensor 124' is displayed, substantially in real-time, on display 126'. The displayed measurement can be numerical or graphical, such as a bar-type or chart recorder-type display.

In a related embodiment, a plurality of different techniques may be used together in a more advanced AED device enabled with MVT. Such devices, with their multiple sensors to engage with the patient, may be more suitable for use by trained rescuers, such as paramedics, for example.

In operation, AED 100 is interfaced with the patient via leads 118a/118b, and MVT effectiveness sensor. In one embodiment, AED 100 provides guidance to a rescuer, via rescuer interface 126, for properly interfacing with the patient. AED 100 measures the patient's condition using monitoring circuitry 122 and at least a portion of the patient interface 116. Next, AED 100 analyzes the measured patient's condition to determine the existence of any indications for treating the patient. If the patient exhibits a condition treatable by AED 100, the device determines the type of therapeutic signal to apply to the patient, and proceeds to apply the treatment. The therapeutic signal can be an MVT signal, CPR prompt, or a defibrillation signal, either of which is delivered via discharge circuit 108 and leads 118a/118b. During a rescue process, AED 100 provides prompting or instructions to a rescuer for facilitating the therapy and for protecting the rescuer's safety.

Speaking generally for both, implantable, and external MVT-equipped electrotherapy devices described above, the controllers, i.e., controller 16, and controller 106, include a processor circuit (e.g., control unit, arithmetic logic unit, registers, cache, etc.), a data storage circuit such as volatile or non-volatile memory for storing program instructions, input/output facilities, etc. In other embodiments, the controllers can be implemented as logic circuits such as field-programmable gate array (FPGA), application-specific integrated circuit, or the like, or as a combination of the two. In any practical implementation, the controller operates according to specially-configured logic. In microprocessor embodiments, the logic can be in the form of program instructions which are read and executed. In fixed hardware embodiments, the logic is defined based on the interconnections of the logic gates.

In various embodiments, a plurality of different MVT waveforms are adapted to force muscular contractions are utilized according to embodiments of the invention. The waveforms are each adapted to repeatedly artificially force and maintain musculature of the patient in a contracted state. Maintaining contraction may or may not be for a time duration sufficient to achieve myocardial perfusion. Upon cessation of each waveform, the targeted musculature relaxes. The time period between the cessation of the MVT and the muscle relaxation varies according to muscle type, can also vary according to each individual patient's size, physical features, or disease state.

The MVT waveforms discussed herein are administered at a higher energy than a pacing pulse, but at a lower energy than a defibrillation pulse. A pacing pulse is adapted to initiate a myocardial cell activation process in the heart, wherein myocardial tissue naturally contracts due to the heart's natural activation wavefront propagation. Pacing merely adjusts natural cardiac activity, such as electrically stimulating cardiac muscles such that they contract synchronously across different regions of the heart. Therefore, a pacing waveform is incapable of electrically forcing and/or maintaining a heart contraction or inducing cardiac perfusion during a cardiac event such as ventricular fibrillation. A defibrillation pulse, on the other hand, involves the delivery of energy sufficient to shock the heart into a "reset state", and is intended to reset the natural electrical activity of the heart. In contrast with pacing and defibrillation pulses, in one embodiment, the MVT waveforms as discussed herein are delivered with sufficient energy to electrically force a cardiac contraction, however without delivering energy intended to perform a cardiac "reset" such as would result from a defibrillation pulse. In various embodiments, the MVT waveforms discussed herein adapted to artificially force and maintain the heart or the chest cavity in a contracted state.

Figure 4A:
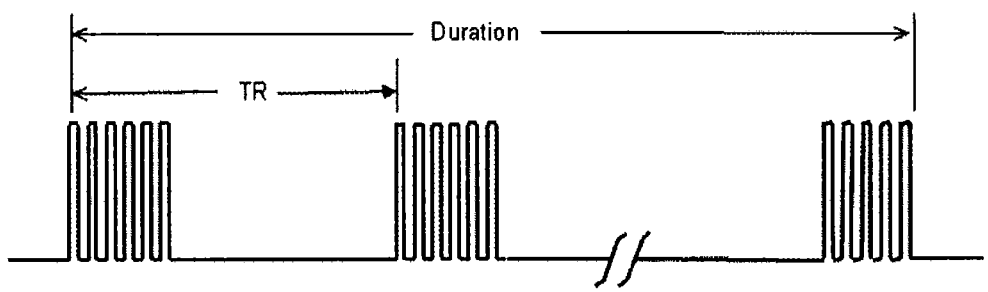
FIGS. 4A-4B are time-domain waveform diagrams illustrating variable parameters of the MVT according to various embodiments of the invention.
Figure 4B:
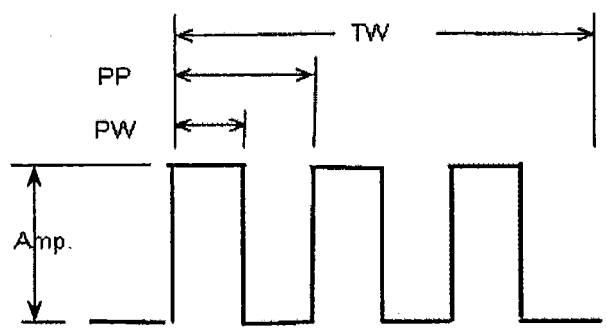

FIG. 4A is a diagram illustrating some of the general parameters of the MVT pulse waveforms The train rate TR can be considered to be the forced "heart rate" in beats per minute, since a pulse packet produces one chest constriction. The duration is the length of time for during which a single session of MVT is applied. FIG. 4B is a diagram detailing a single pulse packet, having parameters of amplitude (AMP), pulse width PW, pulse period PP, and train width TW.

Certain effective parameters have been reported in the following published manuscripts, incorporated by reference herein: "Transthoracic Application Of Electrical Cardiopulmonary Resuscitation For Treatment Of Cardiac Arrest," Crit Care Med, vol. 36, no. 11, pp. s458-66, 2008 and "Coronary Blood Flow Produced by Muscle Contractions Induced by Intracardiac Electrical CPR during Ventricular Fibrillation," PACE vol. 32, pp. S223-7, 2009.

Table 1 below provides an exemplary range of parameter values corresponding to empirically determined effectiveness.

TABLE 1

Exemplary Parameter Value Ranges for MVT

| Parameter | Value of Parameter (Implanted Devices) | Value of Parameter (External Devices) |
| --- | --- | --- |
| MVT Duration | 20-120 sec. | 20-120 sec. |
| Train Rate | 30-120 per min. | 30-120 per min. |
| Pulse Current Amplitude | 0.25-5 A | 0.25-5 A |
| Pulse Voltage Amplitude | 15-250 V | 60-300 V |
| Pulse Width | 0.15-10 ms | 0.15-10 ms |
| Pulse Period | 5-70 ms | 5-70 ms |

In one aspect of the invention, the MVT waveform is tuned to increase selectivity of muscle type in the application of the MVT. Muscle type selectivity permits more precise targeted forced contractions. In one particular embodiment, contractions are separately controlled between the chest musculature (skeletal muscles), and the heart, such that one, the other, or both, may be selectively activated or allowed to relax.

An MVT waveform that is optimized for skeletal muscle capture (OSC) according to one embodiment is adapted to force primarily skeletal muscle contractions. The OSC waveform is adapted to force a contraction and subsequent release of skeletal muscles in order to vary the pressure (and volume) within the chest cavity. Some amount of ventilation can also be achieved due to expanding and contracting of the lungs.

An MVT waveform that is optimized for myocardial capture (OMC) according to a related embodiment is adapted to force cardiac muscle contractions. The OMC waveform is adapted to force contraction of primarily cardiac muscles in order to achieve some level of perfusion for the heart and other vital organs. Tables 2 and 3 below provide exemplary ranges for OSC and OMC MVT parameter values; whereas tables 4 and 5 below provide an exemplary optimal set of values for OSC and OMC waveforms, respectively.

TABLE 2

Example Ranges of Optimal OSC Parameter Values.

| Variable Parameter | Optimal Range |
| --- | --- |
| Pulsed Output Voltage | 75-300 V (external); 20-80 V (implantable) |
| Pulsed Output Current | 1-5 A |
| Pulse Width | .10-.25 ms |
| Pulse Period | 10-20 ms |
| Duration | 10-30 seconds |
| Packet Width | 100-300 ms |
| Train Rate | 80-160 bpm |

TABLE 3

Example Ranges of Optimal OMC Parameter Values.

| Variable Parameter | Optimal Range |
| --- | --- |
| Pulsed Output Voltage | 75-300 V (external); 20-80 V (implantable) |
| Pulsed Output Current | 0.5-5 A |
| Pulse Width | 5-10 ms |
| Pulse Period | 20-40 ms |
| Duration | 10-30 seconds |
| Packet Width | 100-300 ms |
| Train Rate | 80-160 bpm |

TABLE 4

Exemplary Stimulation Waveform for OMC

| Variable Parameter | Optimal Value |
| --- | --- |
| Pulsed Output Voltage | 75-300 V (external); 20-80 V (implantable) |
| Pulsed Output Current | 0.5-1 A |
| Pulse Width | 7.5 ms |
| Pulse Period | 30 ms |
| Duration | 20 seconds |
| Packet Width | 200 ms |
| Train Rate | 120 bpm |

TABLE 5

Exemplary Stimulation Waveform for OSC

| Variable Parameter | Optimal Value |
| --- | --- |
| Pulsed Output Voltage | 75-300 V (external); 20-80 V (implantable) |
| Pulsed Output Current | 2 A |

TABLE 5-continued

Exemplary Stimulation Waveform for OSC

| Variable Parameter | Optimal Value |
|---|---|
| Pulse Width | .15 ms |
| Pulse Period | 15 ms |
| Duration | 20 seconds |
| Packet Width | 200 ms |
| Train Rate | 120 bpm |

In one type of embodiment, the waveform parameters are varied or modulated for different purposes. One such purpose is to enhance or adjust the MVT effectiveness—that is, to vary the hemodynamic and other electrostimulation effects to achieve one or more treatment goals.

One such treatment goal is management of muscle fatigue. MVT stimulation can, in a matter of a few minutes, fatigue the heart or other muscles to a point where they become unresponsive to further stimulation. Accordingly, in this embodiment, the MVT parameters are set or adjusted to minimize, or simply reduce, MVT-induced muscle fatigue, thereby allowing the MVT treatment to be prolonged.

Another treatment goal is to place the heart into a preferred state in which to receive a subsequent defibrillation shock such that the likelihood of success is improved. According to the MVT is administered as a series of repeated, time-coordinated, applications of MVT waveforms to optimized for OSC and OMC. The time coordination of these targeted waveforms permits the chest and heart to be separately placed into respective states to best receive the defibrillation shock. In one such approach, not only is the MVT used for pumping action to maintain the patient's survival during a life-threatening condition such as VF, but the parameters of the MVT are specifically adjusted as the time to administer the defibrillation shock approaches, to improve or optimize the defibrillation effectiveness.

In one embodiment, as the time to defibrillate approaches, the device switches from an OMC to an OSC waveform for stimulating primarily non-cardiac muscles. This gives the heart more time to rest, and to be in a "fresher" state for receiving the defibrillation therapy, which improves the likelihood of successful conversion of the arrhythmia with defibrillation.

In another embodiment, a specific timed sequence of OSC and OMC waveforms is administered. These sequences are specifically designed to establish separate but synchronized compression cycles in the patient's chest, and myocardium, respectively.

In one approach, the OSC waveform is followed immediately by the OMC waveform. In a related approach, not only is the muscle capture and compression effect utilized, but the subsequent release and relaxation of the muscle in response to cessation of an MVT stimulus is used. In a particular example, the thoracic rebound resulting from cessation of OSC stimulation is a condition to which the defibrillation shock is synchronized.

In a related embodiment, the skeletal muscles are stimulated by OSC, and heart is stimulated by OMC during the later part of the OSC stimulation so that the heart remains compressed while the thoracic musculature is relaxed. During this period, the defibrillation shock is administered. In this approach, with the cessation of the thoracic musculature, the chest rebounds in an upstroke, and the lungs take in some air. This state tends to concentrate the conductivity, and therefore the current path for the defibrillation shock, in the region of the heart. At the same time, since the heart remains compressed, which also tends to concentrate the current density of the defibrillation shock in the region of the heart. In another related embodiment, the OMC is terminated at the same time, or just before, the defibrillation shock. This will tend to relax the myocardium and relieve some of the strain experienced by the myocardial cells forced into contraction just in time for the defibrillation shock, but before the heart expands on the rebound part of its compression phase.

Figure 5A:
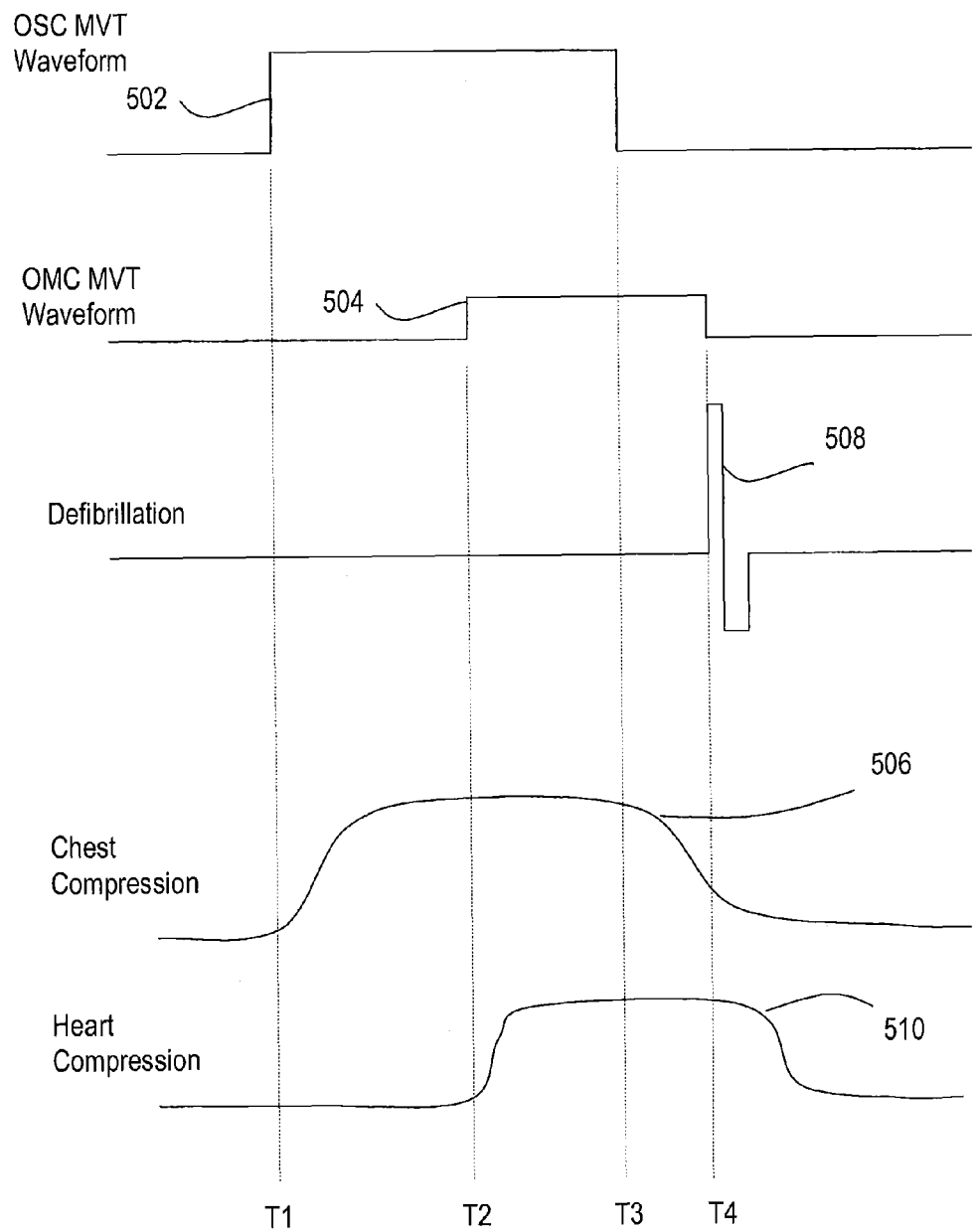
FIGS. 5A-5B are timing and flow diagrams, respectively, that depict an exemplary time-coordinated treatment sequence involving two types of targeted MVT stimulation synchronized with defibrillation therapy according to one embodiment.

FIG. 5A is a timing diagram illustrating an example of a synchronized, or time-coordinated, protocol for administering an MVT sequence followed by a time-coordinated defibrillation shock. An OSC waveform 502 is administrated starting at time T1. In one particular example, The OSC is applied for 200-300 ms to obtain a full chest compression in view of the delays from viscosity and mass interactions. A portion of the chest compression is depicted as curve 506. This is also thought to compress the right ventricle but not the left ventricle. At time T2, which in one example falls within the last 100-150 ms of the OSC waveform, the OMC waveform 504 is administered. This second MVT waveform 504 is superimposed on the OSC waveform such that both regions are stimulated together for the overlapping portion. To minimize the effect that the OMC waveform has on the skeletal muscles, its amplitude (i.e. pulse current) is reduced to 10-50% of the current of the OSC. This will result in a partial contraction of the left ventricle in addition to the right ventricle (thought to also be compressed at this point by the chest compression), but with significantly reduced chest compression effect. The secondary compression cycle related to the heart is depicted as curve 510. At time T3, the OSC stimulation is ceased. The chest will rebound in its upstroke phase of the chest compression cycle.

Time T4 is synchronized to coincide with the end portion of the chest rebound. This can be preset in one embodiment as 100 ms. In related embodiments, the time period T3-T4 is determined for the particular patient from one or more previous MVT cycles. In another embodiment, the time T4 is found in the present cycle based on real-time monitoring of an indicator of the chest compression state (e.g., impedance measurement, pressure measurement, blood flow measurement, etc.), wherein a computation of the time derivative of the monitored indicia can indicate the end of the upstroke phase of the chest compression cycle.

At T4, the OMC is ceased, and the defibrillation pulse 508 is administered. The cessation of the OMC waveform 504 can coincide with the defibrillation shock, or can precede the defibrillation shock by a small amount. In this approach, one feature is that the defibrillation shock is timed to strike the heart when the heart is still compressed, even though the OMC administration may have already ended, thereby taking advantage of the increase in the current density which is associated with this myocardial state. In the embodiment where the OMC is terminated just prior to the defibrillation shock, it is possible that the myocardial cells are relieved of their straining, placing them in better condition to respond favorably to the defibrillation energy.

Figure 5B:
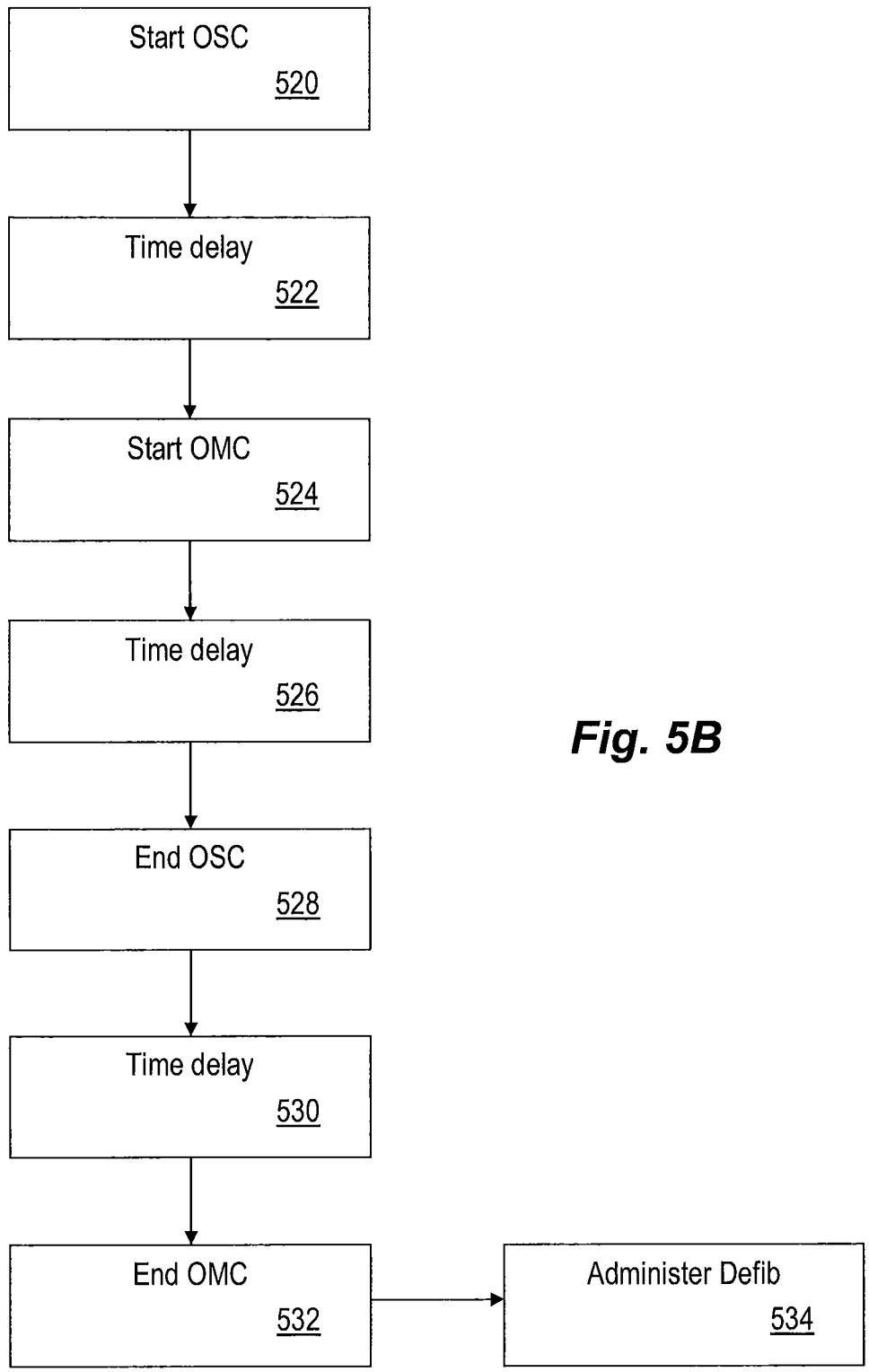
Figure 6:
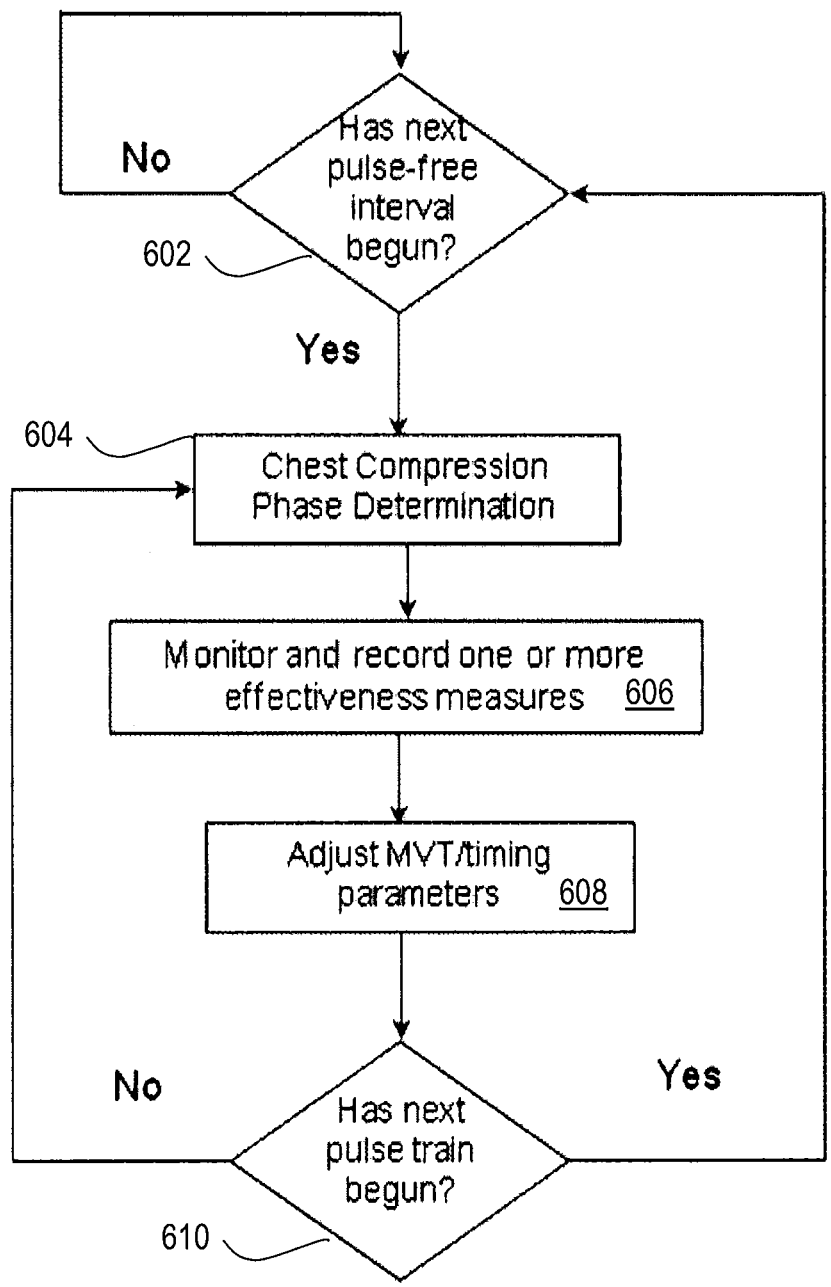
FIG. 6 is a flow diagram representing an exemplary process of adapting MVT or timing parameters in response to chest compression phase and hemodynamic monitoring according to one embodiment.

FIG. 5B is a flow diagram illustrating an exemplary process of administering the time-coordinated MVT-defibrillation therapy according to an embodiment of this type. At 520, the OSC is started. At 522, a time delay is introduced while the pulse packet of the OSC activates and maintains contraction of the skeletal musculature. At 524, OMC is administered, and a time delay at 526 is tracked while both types of MVT are simultaneously applied. At 528, the OSC is terminated, causing the chest to begin to relax, during which time 530, the OMC is maintained. At 532, which in one embodiment corresponds approximately to the end of the chest's relaxation, or slightly before the end, the OMC is terminated, followed immediately, or very close in time, (e.g., <20 ms) by the defibrillation shock at 534. Following this treatment, the cardiac rhythm is re-assessed to determine whether the defibrillation was successful.

In one variation of this embodiment, the time delay 530 (i.e., the time between T3 and T4 in FIG. 5A) is adjusted so that the cessation of the OMC and defibrillation shock delivery is timed to coincide with a different portion of the chest compression rebound. For example, time T4 can be targeted to coincide with the middle of the upstroke phase, or with the beginning of the upstroke phase.

In a related embodiment, in response to an unsuccessful defibrillation attempt, the time delay 530 (i.e., the time between T3 and T4 in FIG. 5A) is adjusted to a different part of the chest compression cycle than in the previous defibrillation attempt. A data structure in the controller can maintain a set of values from which to pick, along with an algorithm according to which successive values are selected for this time delay.

In another type of variation, the defibrillation shock and the OMC cessation are not performed close in time. In fact, the inventors contemplate that other optimal combinations and timings involving time-coordinated OSC stimulation, OMC stimulation, and defibrillation, may be utilized according to future research findings.

In a related embodiment, in devices where nerve stimulation is supported, the MVT is additionally applied to stimulate the phrenic nerve in time-coordinated application with cessation of the OSC stimulation. This can further enhance the chest rebound effect following the chest compression caused by the OSC. In one such approach, the phrenic nerve stimulation is started close in time prior to the defibrillation shock. Thus, the defibrillation is applied at a point where the pressure in the chest cavity is at a minimum value. In another approach, the phrenic nerve stimulation is applied earlier to allow sufficient time for the lungs to expand prior to the defibrillation shock, which may tend to concentrate the defibrillation current path to the heart region. In a related embodiment, these parameters are varied from one defibrillation cycle to another to provide diverse treatments in an effort to successfully defibrillate following a failed attempt.

In another related embodiment, the MVT-enabled implantable or external electrotherapy device uses its hemodynamic monitoring facilities to measure variables such impedance, as blood flow, blood pressure, or blood oxygenation, or a combination thereof, to determine such events as the phase of the chest or myocardial compression cycles, and MVT effectiveness. Using this measured information, the intensity and targeting of the MVT can be adjusted to achieve improved chest compressions, improved hemodynamic responses from MVT, or improved myocardial compressions. In the exemplary embodiment depicted, at 602, the conclusion of an MVT pulse packet is determined. In this window, at 604, the chest compression phase is determined based on one or more physiologic or hemodynamic measurements. At 606, one or more measures are monitored, recorded, and analyzed, from which adjustments can be made according to a set of adjustment rules at 608. At 610, at the beginning of the next pulse train, the determination of the chest compression phase can be further analyzed.

In varying the MVT waveform to improve its effectiveness according to one type of embodiment, for either the OSC, or OMC waveforms, or in another type of MVT waveform which may be non-targeted to muscle groups, the pulse period is modulated during administration of the MVT administration. The degree of modulation can be in the neighborhoods of 5%, 10%, 15%, or more. In one variant of this embodiment, the modulation is randomized, or noise-like. In another embodiment, the modulation is applied with a certain pattern (i.e., with a predetermined modulating signal), or with a certain combination of patterns, which can be alternated based on randomization or based on one or more alternation functions. Modulation of the pulse period in any of these fashions may help to recruit more muscle fibers than a MVT signal with non-modulated pulse period, and may reduce or delay the onset of muscle fatigue caused by MVT. Additionally, the modulation of pulse period may enhance the hemodynamic effect, which in turn permits a reduction in pulse amplitude for an equivalent hemodynamic output or sympathetic stimulation effect. The modulation may also affect the relative timing of the compression cycle triggered by the MVT.

Figure 7:
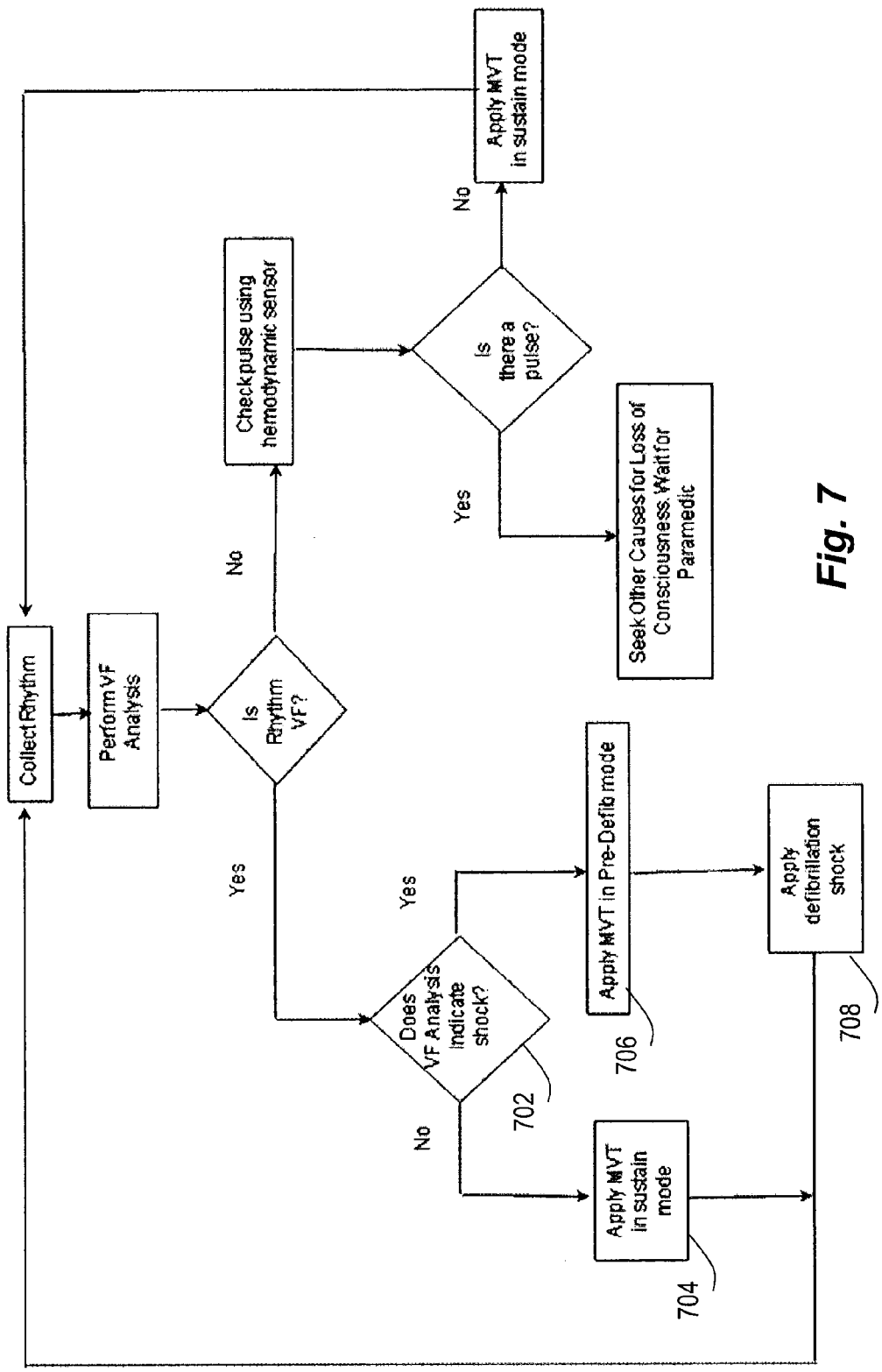
FIG. 7 is a flow diagram illustrating an exemplary rescue process in which an electrotherapy device utilizes MVT in sustain mode, and MVT in pre-defibrillation mode, according to one type of embodiment.

FIG. 7 is a diagram illustrating an exemplary rescue process that can be carried out by either an implantable device, or an external AED-type device. Notably, upon determination of a VF rhythm, at 702, an analysis is made as to whether a defibrillation shock is indicated for the particular rhythm. If not, then MVT is indicated. This MVT, which is performed at 704, is adapted for sustaining the life of the patient, i.e., analogous to CPR. The rhythm is re-analyzed subsequent to this MVT treatment. If defibrillation is indicated, the defibrillation is preceded by MVT in pre-defibrillation mode along the lines described above to place the chest and heart into the best compression cycle state according to the present circumstances and to rules that the device is programmed to apply. This pre-treatment MVT is administered at 706, and is followed by a time-coordinated defibrillation shock at 708. In the event of a failure to defibrillate, the MVT parameters for the pre-defibrillation MVT are adjusted for the next attempt.

In a further aspect of the invention, the various electrodes described above for MVT administration can be selectively switched in and out of the pulse generating circuitry, enabling selective application of MVT to specific regions of the body (corresponding to specific muscles or muscle groups). Table 6 below lists various exemplary muscles that are individually targeted in one type of embodiment.

TABLE 6

Exemplary Muscles Targeted through Specific MVT Electrode Placement

| Muscle ID | Muscle Description |
|---|---|
| A | Heart |
| B | Right Pectoral |
| C | Left Pectoral |
| D | Right Intercostals |
| E | Left Intercostals |
| F | Right Abdominals |
| G | Left Abdominals |
| H | Back - left side |
| I | Back - right side |

In one type of embodiment according to this aspect of the invention, the targeting of muscles is automatically coordinated and varied based on changing circumstances, by the MVT-enabled device, to achieve a desired therapeutic effect based on the monitored patient condition, including the type of arrhythmia, the hemodynamic effect of applied MVT, and on the specific treatment or rescue algorithm being administered. In a related embodiment, the targeting of specific muscles is coordinated with the MVT waveform to be applied to further enhance the specificity of the MVT targeting.

One example of the desired therapeutic effect is management of muscle fatigue. In a corresponding embodiment, certain muscles are stimulated by MVT for longer or shorter durations based on that muscle's endurance of MVT. In a related embodiment, muscle groups having left and right sides, i.e., pectorals, intercostals, abdominals, are stimulated such that only one side at a time is activated by MVT, allowing the other side to rest and recuperate. Variation of muscle selection can be predetermined according to a programmed algorithm which is selected in response to the detected type of arrhythmia. Alternatively, to account for variation among patients, selection of muscles for stimulation is made in response to hemodynamic monitoring.

In one embodiment, the controller of the MVT circuit maintains a one or more data structures that relate the different muscles for which the device is configured to stimulate via MVT, to amplitude and waveform parameter information corresponding to that muscle group. In a related embodiment, the data structure(s) further include associations between treatment algorithms corresponding to various arrhythmias or patient conditions, as measured by the patient monitoring facilities of the device, and MVT parameter values to use for those arrhythmias or conditions.

In one example, the device is programmed to apply relatively higher intensity MVT to one type of muscle group (or one side of the body) than to another muscle group or side of the body as a test of endurance of the patient's musculature to MVT. The other side, which is less intensely stimulated, may then remain available for longer-duration MVT therapy.

In a related embodiment, if defibrillation is unsuccessful following the standard protocol of 4-6 shocks, the MVT for both, the heart and the skeletal muscle, is automatically adjusted to their respective low-intensity modes so that the patient's life support can be prolonged with MVT. This becomes essentially a muscle fatigue management (and device energy conservation) strategy.

Figure 8:
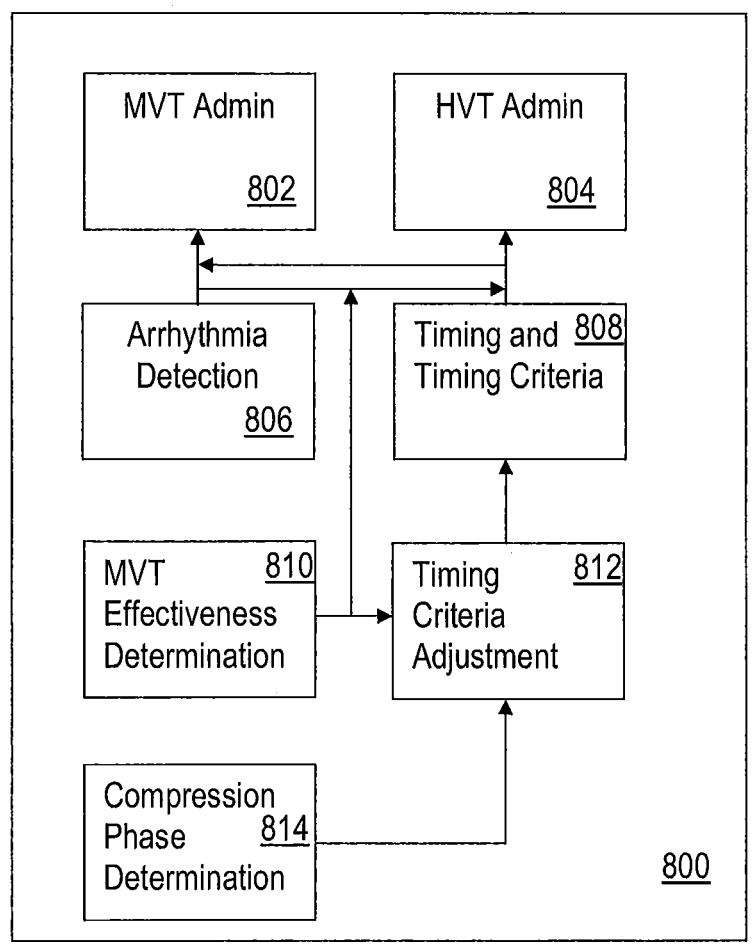
FIG. 8 is a block diagram illustrating some of the logic modules implemented in a controller of an electrotherapy device according to one embodiment.

FIG. 8 is a block diagram of several exemplary logic modules implemented in the controller 800 of an electrotherapy device according to certain embodiments. MVT administration logic controls the various forms of MVT that can be administered to the patient. High-voltage therapy administration logic 804 controls the delivery of the defibrillation, which can also have a variable waveform. In one embodiment, HVT administration logic is further configured to cause the electrotherapy circuitry to administer the HVT based on the relative timing between the reference point and the at least one target point, such that the administration of the HVT is synchronized with the administration of the MVT based on the relative timing determined by the compression phase determining logic, and wherein to achieve that synchronization a timing of the HVT is varied in response to variation of the relative timing.

Arrhythmia detection logic 806 receives input the rhythm monitoring circuit and provides this information to the MVT and high-voltage therapy logic modules 802 and 804. Modules 802 and 804 operate to achieve the time-coordinated electrotherapy sequencing discussed above based on timing criteria and timing mechanism module 808, which provides instructions on how to coordinate the various electrotherapy modalities. The timing criteria, being adaptive according to certain embodiments, is adjusted by timing criteria adjustment logic module 812, which in turn receives inputs from MVT effectiveness determination logic 810, and compression phase determination logic 814. Each of these modules 810, 814 receive input from hemodynamic or physiologic monitoring circuitry, which is itself interfaced with one or more sensors for measuring suitable indicia such as those discussed above.

Compression phase determination logic, in one embodiment, maintains at least one data structure that defines various phases of the compression cycle, and that relates at least one target point in the compression cycle of the target region to one particular phase of the compression cycle. This target point may be a point to which the defibrillation shock is synchronized, or referenced to with either some time offset, or directly. In another embodiment, the compression phase determination logic maintains at least one data structure that associates various indicia of degree of compression of the target region with various phases of the compression cycle, and that relates the at least one target point in the compression cycle of the target region to one particular phase of the compression cycle.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An electrotherapy device for treating cardiac arrhythmia in a patient, the device comprising:
   electrotherapy circuitry operatively coupled to a patient interface and including:
      a medium voltage therapy (MVT) circuit constructed to administer a MVT via the patient interface to each of a plurality of target regions of the patient, the MVT having an insufficient energy level to shock the heart into a reset state, but having an energy level and a variable waveform that causes musculature in each corresponding target region to be (a) electrically activated into a contracted state, (b) electrically maintained in the contracted state for a compression duration, and (c) thereafter allowed to relax, thereby achieving a forced compression and release of that target region, wherein the plurality of target regions includes a first target region having primarily skeletal musculature, and a second target region having primarily myocardial musculature; and a high voltage therapy (HVT) circuit constructed to administer a HVT via the patient interface, wherein the HVT is of an energy level sufficient to shock the heart into a reset state; and a controller circuit operatively coupled to the patient monitoring circuitry and the electrotherapy circuitry, the controller circuit programmed to, in response to a detection of a presence of an arrhythmia treatable by the HVT:

cause the electrotherapy circuitry to administer the MVT, and cause the electrotherapy circuitry to administer the HVT in coordination with administration of the MVT.

2. The electrotherapy device of claim 1, wherein the patient interface includes a plurality of electrodes, each electrode configured to be positioned in electrical contact with the patient.

3. The electrotherapy device of claim 1, wherein the controller circuit is further programmed to cause the electrotherapy circuitry to administer the MVT as a series of repeated, time-coordinated, applications of a first MVT waveform to the first target region and a second MVT waveform to the second target region.

4. The electrotherapy device of claim 3, wherein the controller circuit is further programmed to cause the electrotherapy circuitry to administer the HVT in time-coordinated response to the applications of the MVT, such that the HVT is synchronized relative to (a) a first compression cycle corresponding to activation of the first target region, and (b) a second compression cycle corresponding to activation of the second target region, resulting from the administration of the MVT.

5. The electrotherapy device of claim 3, wherein the sequence of the time-coordinated applications of the MVT includes the first MVT waveform, followed immediately by the second MVT waveform.

6. The electrotherapy device of claim 5, wherein the second MVT waveform has an amplitude between 10% and 50% of the first MVT waveform.

7. The electrotherapy device of claim 5, wherein the first MVT waveform is applied for a duration of between 200 and 300 milliseconds and wherein the second MVT waveform is applied for a duration of between 200 and 250 milliseconds and initiated during the last 100-150 milliseconds of the first MVT waveform.

8. The electrotherapy device of claim 1, further comprising a patient monitoring circuitry including an arrhythmia monitoring circuit, the patient monitoring circuitry operatively coupled to the patient interface.

9. The electrotherapy device of claim 1, the MVT circuit constructed to administer a MVT via the patient interface to each of a plurality of target regions of the patient, wherein the plurality of target regions includes a first target region having primarily skeletal musculature, and a second target region having primarily myocardial musculature.

10. An electrotherapy device for treating cardiac arrhythmia in a patient, the device comprising:

electrotherapy circuitry operatively coupled to a patient interface and including:

a medium voltage therapy (MVT) circuit constructed to administer a MVT via the patient interface to each of a plurality of target regions of the patient; and a high voltage therapy (HVT) circuit constructed to administer a HVT via the patient interface; and a controller circuit operatively coupled to the patient monitoring circuitry and the electrotherapy circuitry, the controller circuit programmed to, in response to a detection of a presence of an arrhythmia treatable by the HVT:

cause the electrotherapy circuitry to administer the MVT, the MVT having an insufficient energy level to shock the heart into a reset state but having an energy level and a variable waveform that causes musculature in each corresponding target region to be (a) electrically activated into a contracted state, (b) electrically maintained in the contracted state for a compression duration, and (c) thereafter allowed to relax, thereby achieving a forced compression and release of that target region, wherein the plurality of target regions includes a first target region having primarily skeletal musculature, and a second target region having primarily myocardial musculature; and cause the electrotherapy circuitry to administer the HVT in coordination with administration of the MVT, wherein the HVT is of an energy level sufficient to shock the heart into a reset state.

11. The electrotherapy device of claim 8, wherein the patient interface includes a plurality of electrodes, each electrode configured to be positioned in electrical contact with the patient.

12. The electrotherapy device of claim 10, wherein the controller circuit is further programmed to cause the electrotherapy circuitry to administer the MVT as a series of repeated, time-coordinated, applications of a first MVT waveform to the first target region and a second MVT waveform to the second target region.

13. The electrotherapy device of claim 12, wherein the controller circuit is further programmed to cause the electrotherapy circuitry to administer the HVT in time-coordinated response to the applications of the MVT, such that the HVT is synchronized relative to (a) a first compression cycle corresponding to activation of the first target region, and (b) a second compression cycle corresponding to activation of the second target region, resulting from the administration of the MVT.

14. The electrotherapy device of claim 12, wherein the sequence of the time-coordinated applications of the MVT includes the first MVT waveform, followed immediately by the second MVT waveform.

15. The electrotherapy device of claim 14, wherein the second MVT waveform has an amplitude between 10% and 50% of the first MVT waveform.

16. The electrotherapy device of claim 14, wherein the first MVT waveform is applied for a duration of between 200 and 300 milliseconds and wherein the second MVT waveform is applied for a duration of between 200 and 250 milliseconds and initiated during the last 100-150 milliseconds of the first MVT waveform.

17. The electrotherapy device of claim 10, further comprising a patient monitoring circuitry including an arrhythmia monitoring circuit, the patient monitoring circuitry operatively coupled to the patient interface.

18. The electrotherapy device of claim 10, the MVT circuit constructed to administer a MVT via the patient interface to each of a plurality of target regions of the patient, wherein the plurality of target regions includes a first target region having primarily skeletal musculature, and a second target region having primarily myocardial musculature.

19. A method, comprising:
    providing an electrotherapy device to a user; and
    providing instructions recorded on a tangible medium to the user, the instructions including:
        causing the electrotherapy device to initiate operation, the electrotherapy device configured to:
            administer medium voltage therapy (MVT) as a series of repeated, time-coordinated, applications of MVT waveforms to first and second target regions of a patient in response to a detection of a presence of an arrhythmia treatable by high-voltage therapy (HVT) based on automated patient monitoring by the electrotherapy device, wherein the first target region has primarily skeletal musculature and the second target region has primarily myocardial musculature; and
            administer the HVT in response to the detection of the presence of the arrhythmia treatable by the HVT, and in time-coordinated response to a sequence of the time-coordinated applications of the MVT;
        wherein the time-coordinated applications of the MVT include a first MVT waveform to the first target region and a second MVT waveform to the second target region, such that the HVT is synchronized relative to at least one of: (a) a first compression cycle corresponding to activation of the first target region, and (b) a second compression cycle corresponding to activation of the second target region, resulting from the administration of the MVT.

* * * * *